US006756376B1

(12) United States Patent
Fuji et al.

(10) Patent No.: US 6,756,376 B1
(45) Date of Patent: Jun. 29, 2004

(54) TRICYCLIC AZAINDOLIZINE DERIVATIVES HAVING AN SPLA$_2$-INHIBITORY ACTIVITIES

(75) Inventors: Masahiro Fuji, Osaka (JP); Tetsuo Okada, Osaka (JP); Makoto Adachi, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 48 days.

(21) Appl. No.: 10/129,658

(22) PCT Filed: Nov. 10, 2000

(86) PCT No.: PCT/JP00/07907

§ 371 (c)(1),
(2), (4) Date: May 9, 2002

(87) PCT Pub. No.: WO01/36420

PCT Pub. Date: May 25, 2001

(30) Foreign Application Priority Data

Nov. 15, 1999 (JP) ............................................ 11/323884

(51) Int. Cl.$^7$ .................. C07D 487/04; A61K 31/4985; A61K 31/5025
(52) U.S. Cl. ........................ 514/248; 514/248; 544/234; 544/344
(58) Field of Search ................................ 514/248, 250; 544/234, 344

(56) References Cited

U.S. PATENT DOCUMENTS 2,791,562 A * 5/1957 Diffley ........................ 510/536

FOREIGN PATENT DOCUMENTS

| EP | 0 620 214 A1 | 10/1994 |
|---|---|---|
| EP | 0 620 215 A1 | 10/1994 |
| EP | 0 675 110 A1 | 10/1995 |
| WO | WO 96/03120 A1 | 2/1996 |
| WO | WO 96/03376 A1 | 2/1996 |
| WO | WO 96/03383 A1 | 2/1996 |
| WO | WO 97/21664 A1 | 6/1997 |
| WO | WO 97/21716 A1 | 6/1997 |
| WO | WO 98/18464 A1 | 5/1998 |
| WO | WO 99/51605 A1 | 10/1999 |

OTHER PUBLICATIONS

Wolff, Manfred E. "Burger's Medicinal Chemistry, 5ed, Part I", John Wiley & Sons, 1995, pp. 975–977.*
Banker, G.S. et al, "Modern Pharmaceutics, 3ed.", Marcel Dekker, New York, 1996, p. 596.*
Lehr, M., Expert Opin. Ther. Patents, vol. 11, 2001, pp. 1125–1156.*
Tanaka, K et al, Agents Actions Suppl., vol. 46, 1995, pp. 51–64.*
Scott, K.F. et al, Expert Opin. Ther. Targets, vol. 7, 2003, pp. 427–440.*
Tibes, U. et al, Expert Opin. Invest. Drugs, vol. 6, 1997, pp. 279–298.*
Blanchard, S.G. et al, Pharm. Biotechnol., Chapter 19, vol. 11, 1998, pp. 445–463.*

Matsumoto, Kiyoshi et al., "1,3–Dipolar Cycloaddition Reactions of Cyclooctyne with Pyridinium Dicyanomethylides," J. Heterocycl. Chem., (1997), vol. 34, No. 1, pp. 203–208.
Matsumoto, Kiyoshi et al., "1,3–Dipolar Cycloaddition Reactions of Cyclooctyne with Azomethine Ylides," J. Heterocycl. Chem., (1995), vol. 32, No. 1, pp. 367–369.
Cupillard et al., "Cloning, Chromosomal Mapping, and Expression of a Novel Human Secretory Phospholipase A$_2$", The Journal of Biological Chemistyr, vol. 272, No. 25, Jun. 20, pp. 15745–15752, 1997, by the American Society for Biochemistry and Molecular Biology, Inc., USA.
Chen et al., "Cloning and Recombinant Expression of a Novel Human Low Molecular Weight Ca$^{2+}$– dependent Phospholipase A$_2$", The Journal of Biological Chemistry, vol. 269, No. 4, Jan. 28, 1994, pp. 2365–2368, by the American Society for Biochemistry and Molecular Biology, Inc., Palo Alto, California.
Kanda, et al., "Characterization of recombinant human and rat pancreatic phospholipases A$_2$ secreted from Saccharomyces cerevisiae: difference in proteolytic processing", Biochimica et Biophysica Acta, 1171 (1992) 1–10, 1992, Elsevier Science Publishers B.V., Osaka, Japan.
Reynolds, et al., "Analysis of Human Synovial Fluid Phospholipase A$_2$ on Short Chain Phosphatidylcholine–Mixed Micelles: Development of a Spectrophotometric Assay Suitable for a Microtiterplate Reader", Analytical Biochemistry, 204, 190–197 (1992), by Academic Press, Inc., La Jolla, California.
Matsumoto, et al., "1,3–Dipolar Cycloaddition Reactions of Cyclooctyne with Azomethine Ylides", J. Heterocyclic Chem., vol. 32, 367–369 (1995), Kyoto, Japan.
Matsumoto, et al., "1,3–Dipolar Cycloaddition Reactions of Cyclooctyne with Pyridinium Dicynomethylides", J. Heterocyclic Chem., vol. 34, 203–208 (1997), Kyoto, Japan.

* cited by examiner

Primary Examiner—Richard L. Raymond
Assistant Examiner—Thomas McKenzie
(74) Attorney, Agent, or Firm—Foley and Lardner

(57) ABSTRACT

The present invention provides a compound having sPLA$_2$ inhibiting activity.

The compound represented by the formula (I):

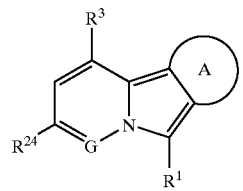

(I)

wherein E is N or C—R$^4$; G is N or C—R$^{25}$; R$^1$ is a carbocyclic group, heterocyclic group or the like; one of R$^3$ and R$^4$ is —(L$^2$)-(acidic group), the other is a hydrogen atom, wherein L$^2$ is a group connecting with an acid group; A ring is optionally substituted 5–8 membered cyclohexane ring or cyclohexene ring; R$^{24}$ and R$^{25}$ are a hydrogen atom or the like, its prodrug, their pharmaceutically acceptable salt, or hydrate thereof.

10 Claims, No Drawings

TRICYCLIC AZAINDOLIZINE DERIVATIVES HAVING AN SPLA$_2$-INHIBITORY ACTIVITIES

DESCRIPTION

Tricyclic azaindolizine derivatives having an sPLA$_2$-inhibitory activities

1. Technical Field

The present invention relates to tricyclic azaindolizine derivatives effective for inhibiting sPLA$_2$-mediated fatty acid release.

2. Background Art sPLA$_2$ (secretory phospholipase A$_2$) is an enzyme that hydrolyzes membrane phospholipids and has been considered to be a rate-determining enzyme that governs the so-called arachidonate cascade where arachidonic acid, the hydrolysis product, is the starting material. Moreover, lysophospholipids that are produced as by-products in the hydrolysis of phospholipids have been known as important mediators in cardiovascular diseases. Accordingly, in order to normalize excess functions of the arachidonate cascade and the lysophospholipids, it is important to develop compounds which inhibit the liberation of sPLA$_2$-mediated fatty acids (for example, arachidonic acid), namely, compounds which inhibit the activity or production of sPLA$_2$. Such compounds are useful for general treatment of symptoms, which are induced and/or sustained by an excess formation of sPLA$_2$, such as septic shock, adult respiratory distress syndrome, pancreatitis, injury, bronchial asthma, allergic rhinitis, chronic rheumatism, arteriosclerosis, cerebral apoplexy, cerebral infarction, inflammatory colitis, psoriasis, cardiac insufficiency, cardiac infarction, and so on. The participation of sPLA$_2$ is considered to be extremely wide and, besides, its action is potent.

As examples of sPLA$_2$ inhibitors are described indole derivatives [EP-620214 (JP Laid-Open No. 010838/95), EP-620215 (JP Laid-Open No. 025850/95), EP-675110 (JP Laid-Open No. 285933/95), and WO 96/03376], indene derivatives (WO 96/03120), indolizine derivatives (WO 96/03383), naphtyl derivatives (WO 97/21664 and WO 9721716), and carbazole derivatives (WO 98/18464), pyrazine derivatives (WO99/51605), and the like.

DISCLOSURE OF INVENTION

The object of the present invention is to provide tricyclic azaindolizine derivatives having sPLA$_2$-inhibitory activities and being useful for treatment of septic shock, adult respiratory distress syndrome, pancreatitis, injury, bronchial asthma, allergic rhinitis, chronic rheumatism, arteriosclerosis, cerebral apoplexy, cerebral infarction, inflammatory colitis, psoriasis, cardiac insufficiency, and cardiac infarction.

The present invention relates to I) a compound represented by the formula (I):

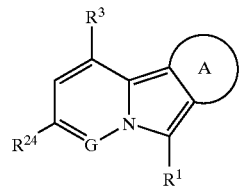

(I)

wherein E is N or C—$R^4$;
when E is N, G is C—$R^{25}$, or when E is C—$R^4$, G is N;
$R^1$ is a group selected from (a) C1 to C20 alkyl, C1 to C20 alkenyl, C1 to C20 alkynyl, carbocyclic groups, and heterocyclic groups, (b) the groups represented by (a) each substituted independently with at least one group selected from non-interfering substituents, or (c) —($L^1$)—$R^5$ wherein $L^1$ is a divalent linking group of 1 to 18 atom(s) selected from hydrogen atom(s), nitrogen atom(s), carbon atom(s), oxygen atom(s), and sulfur atom(s), and $R^5$ is a group selected from the groups (a) and (b);
one of $R^5$ and $R^4$ is —($L^2$)-(acidic group) wherein $L^2$ is an acid linker having an acid linker length of 1 to 6 and the other is a hydrogen atom;
A ring is a group represented by the formula:

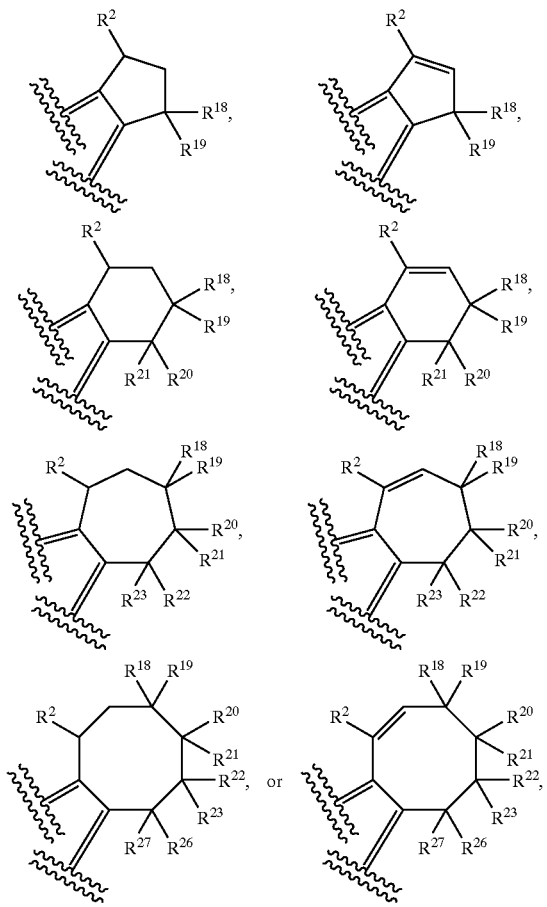

wherein $R^2$ is $CONH_2$, $CONHNH_2$ or $CSNH_2$;
$R^{18}$, $R^{19}$, $R^{20}$, $R^{21}$, $R^{22}$, $R^{23}$, $R^{26}$, and $R^{27}$ are each independently a hydrogen atom, or lower alkyl;
$R^{24}$ and $R^{25}$ are each independently a hydrogen atom, C1 to C6 alkyl, aryl, a halogen or aralkyl;

its prodrug, their pharmaceutically acceptable salt, or hydrate thereof.

In more detail, the present invention relates to II)–XVI).

II) A compound represented by the formula (II):

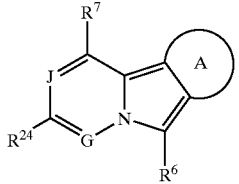
(II)

wherein $R^{24}$ and A ring are as defined above;
J is N or C—$R^8$; when J is N, G is C—$R^{25}$ (wherein $R^{25}$ is as defined above), or when
J is C—$R^8$, G is N;
$R^6$ is —$(CH_2)_m$—$R^9$ wherein m is an integer from 1 to 6, and $R^5$ is (d) a group represented by the formula:

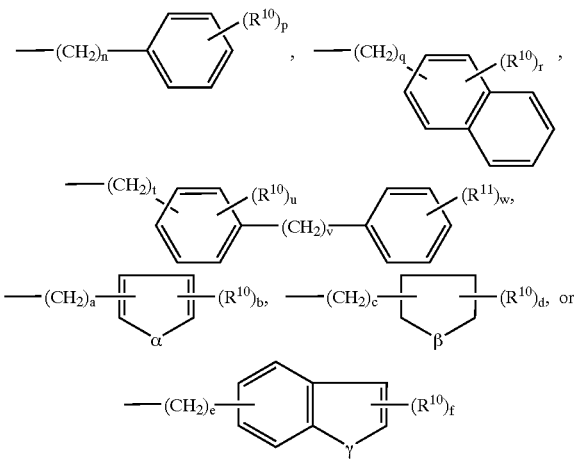

wherein a, c, e, n, q, t and v are each independently 0, 1, or 2; $R^{10}$ and $R^{11}$ are each independently selected from a halogen, C1 to C10 alkyl, C1 to C10 alkyloxy, C1 to C10 alkylthio, optionally substituted phenyl, and C1 to C10 haloalkyl; α is an oxygen atom or a sulfur atom; β is —$CH_2$— or —$(CH_2)_2$—; γ is an oxygen atom or a sulfur atom; b is an integer from 0 to 3, d is an integer from 0 to 4; f, p, and w are each independently an integer from 0 to 5; r is an integer from 0 to 7; and u is an integer from 0 to 4, or $R^9$ is (e) a member of (d) substituted with at least one substituent selected from the group consisting of C1 to C6 alkyl, C1 to C6 alkyloxy, C1 to C6 haloalkyloxy, C1 to C6 haloalkyl, phenyl, and a halogen;
one of $R^7$ and $R^5$ is hydrogen and the other is —$(L^3)$—$R^{12}$ wherein $L^3$ is represented by the formula:

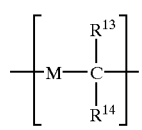

wherein M is —$CH_2$—, —O—, —$N(R^{15})$—, or —S—; $R^{13}$ and $R^{14}$ are each independently a hydrogen atom, C1 to C10 alkyl, aryl, aralkyl, carboxy, or a halogen, and $R^{15}$ is a hydrogen atom or C1 to C6 alkyl; and $R^{12}$ is represented by the formula:

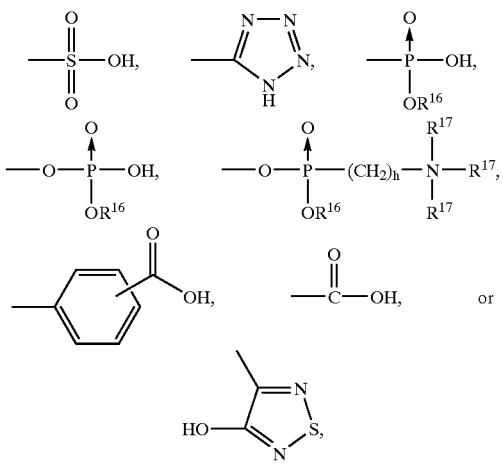

wherein $R^{16}$ is a hydrogen atom, a metal, or C1 to C10 alkyl; $R^{17}$ is independently a hydrogen atom or C1 to C10 alkyl; h is an integer from 1 to 8; its prodrug, their pharmaceutically acceptable salt, or hydrate thereof.

When the above b, d, f, p, r, u, and/or w are 2 or more, a plural number of $R^{10}$ or $R^{11}$ may be different from one another. When $R^{10}$ is a substituent on the naphthyl group, the substituent may substitute at any arbitrary position on the naphthyl group. —$CH_2$— and —$(CH_2)_2$— in β may be substituted with $R^{10}$.

III) A compound, its prodrug, their pharmaceutically acceptable salt, or hydrate thereof as claimed in I) or II), wherein $R^1$ and $R^6$ are represented by the formula:

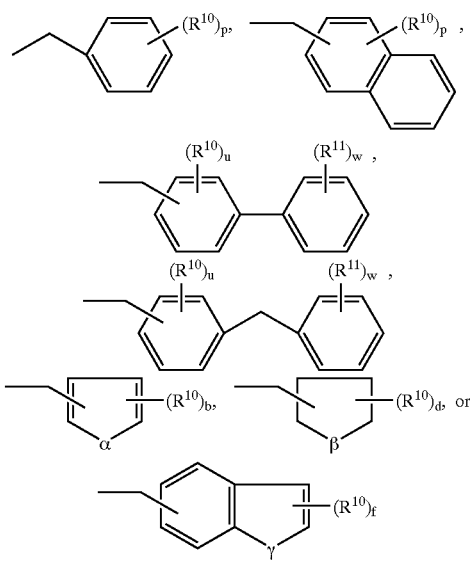

wherein $R^{10}$, $R^{11}$, b, d, f, p, r, u, w, α, β, and γ are as defined above.

When the above b, d, f, p, r, u, and/or w are 2 or more, a plural number of $R^{10}$ or $R^{11}$ may be different from one another. When $R^{10}$ is a substituent on the naphthyl group, the substituent may substitute at any arbitrary position on the naphthyl group. —$CH_2$— and —$(CH_2)_2$— in β may be substituted with $R^{10}$.

IV) A compound, its prodrug, their pharmaceutically acceptable salt, or hydrate thereof as claimed in any one of I) to III), wherein $R^{11}$ and $R^6$ are represented by the formula:

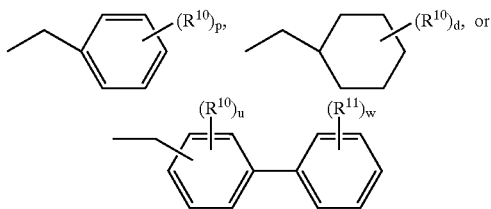

wherein $R^{10}$, $R^{11}$, d, p, u, and w are as defined above.

When the above p, u, and/or w are 2 or more, a plural number of $R^{10}$ or $R^{11}$ may be different from one another.

V) A compound, its prodrug, their pharmaceutically acceptable salt, or hydrate thereof as claimed in any one of I) to IV), wherein $R^3$ and $R^7$ are —O—$(CH_2)_m$—COOH (m is as defined above) or —O—CH(—$R^{30}$)—COOH ($R^{30}$ is a hydrogen atom or C1–C3 alkyl).

VI) A compound represented by the formula (III):

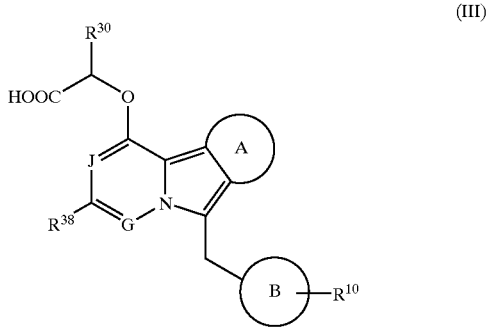

wherein G, J, $R^{10}$, $R^{30}$, A ring, and m are as defined above; B ring is a benzene ring or a cyclohexane ring; $R^{38}$ is hydrogen atom or C1–C3 alkyl, its prodrug, their pharmaceutically acceptable salt, or hydrate thereof.

VII) A compound, its prodrug, their pharmaceutically acceptable salt, or hydrate thereof as claimed in any one of I) to VI), wherein said $R^2$ is —$CONH_2$.

VIII) A compound, its prodrug, their pharmaceutically acceptable salt, or hydrate thereof as claimed in any one of I) to VII), wherein $R^{18}$, $R^{19}$, $R^{20}$, $R^{21}$, $R^{22}$, and $R^{23}$ are hydrogen atoms.

IX) A pharmaceutical composition containing a compound as claimed in any one of I) to VIII) as an active ingredient.

X) A pharmaceutical composition as claimed in IX), which is for inhibiting $sPLA_2$.

XI) A pharmaceutical composition as claimed in IX), which is for inhibiting type I $sPLA_2$.

XII) A pharmaceutical composition as claimed in IX), which is for inhibiting type II $sPLA_2$.

XIII) A pharmaceutical composition as claimed in IX), which is for inhibiting type V $sPLA_2$.

XIV) A pharmaceutical composition as claimed in IX), which is for inhibiting type X $sPLA_2$.

XV) Use of a compound of any one of I) to VIII) for preparation of a pharmaceutical composition for treating diseases caused by $sPLA_2$.

XVI) A method for treating a mammal, including a human, to alleviate the pathological effects of diseases caused by $sPLA_2$, which comprises administration to said mammal of a compound described in any one of I) to VIII) in a pharmaceutically effective amount.

In the present specification, the term "alkyl" employed alone or in combination with other terms means a straight- or branched chain monovalent hydrocarbon group having a specified number of carbon atoms. An example of the alkyl includes methyl, ethyl, n-propyl, isopropyl, n-butyl, isobutyl, sec-butyl, tert-butyl, n-pentyl, n-hexyl, n-heptyl, n-octyl, n-nonyl, n-decanyl, n-undecanyl, n-dodecanyl, n-tridecanyl, n-tetradecanyl, n-pentadecanyl, n-hexadecanyl, n-heptadecanyl, n-octadecanyl, n-nonadecanyl, n-eicosanyl and the like.

The term "alkenyl" employed alone or in combination with other terms in the present specification means a straight- or branched chain monovalent hydrocarbon group having a specified number of carbon atoms and at least one double bond. An example of the alkenyl includes vinyl, allyl, propenyl, crotonyl, isopentenyl, a variety of butenyl isomers and the like.

The term "alkynyl" used in the present specification means a straight or branched chain monovalent hydrocarbon group having a specified number of carbon atoms and at least one triple bond. The alkynyl may contain (a) double bond(s). An example of the alkynyl includes ethynyl, propynyl, 6-heptynyl, 7-octynyl, 8-nonynyl and the like.

The term "carbocyclic group" used in the present specification means a group derived from a saturated or unsaturated, substituted or unsubstituted 5 to 14 membered, preferably 5 to 10 membered, and more preferably 5 to 7 membered organic nucleus whose ring forming atoms (other than hydrogen atoms) are solely carbon atoms. A group containing two to three of the carbocyclic group is also included in the above stated group. An example of typical carbocyclic groups includes (f) cycloalkyl (such as cyclopropyl, cyclobutyl, cyclopentyl, cyclohexyl, cycloheptyl, and cyclooptenyl); cycloalkenyl (such as cyclobutylenyl, cyclopentenyl, cyclohexenyl, cycloheptenyl, and cyclooctenyl); phenyl, naphthyl, norbornyl, bicycloheptadienyl, indenyl, stilbenyl, terphenylyl, phenylcyclohexenyl, acenaphthyl, anthoryl, biphenylyl, bibenzylyl, and a phenylalkylphenyl derivative represented by the formula (IV):

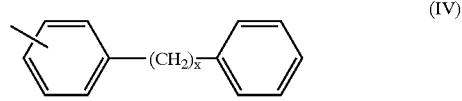

wherein x is an integer from 1 to 8.

The term "heterocyclic group" used in the present specification means a group derived from monocyclic or polycyclic, saturated or unsaturated heterocyclic nucleus having 6 to 14 ring atoms and containing 1 to 3 hetero atoms selected from the group consisting of nitrogen atom, oxygen atom, and sulfur atom. An example of the heterocyclic group includes pyridyl, pyrrolyl, furyl, benzofuryl, thienyl, benzothienyl, pyrazolyl, imidazolyl, phenylimidazolyl, triazolyl, isoxazolyl, oxazolyl, thiazolyl, thiadiazolyl, indolyl, carbazolyl, norharmanyl, azaindolyl, benzofuranyl, dibenzofuranyl, benzotriazolyl, anthranilyl, 1,2-benzisoxazolyl, benzoxazolyl, benzothiazolyl, purinyl, puridinyl, dipyridinyl, phenylpyridinyl, benzylpyridinyl, pyrimidinyl, phenylpyrimidinyl, pyrazinyl, 1,3,5-triazinyl, quinolyl, phthalazinyl, quinazolinyl, quinoxalinyl and the like.

Preferred carbocyclic and heterocyclic groups in $R^1$ are
(g) a group represented by the formula:

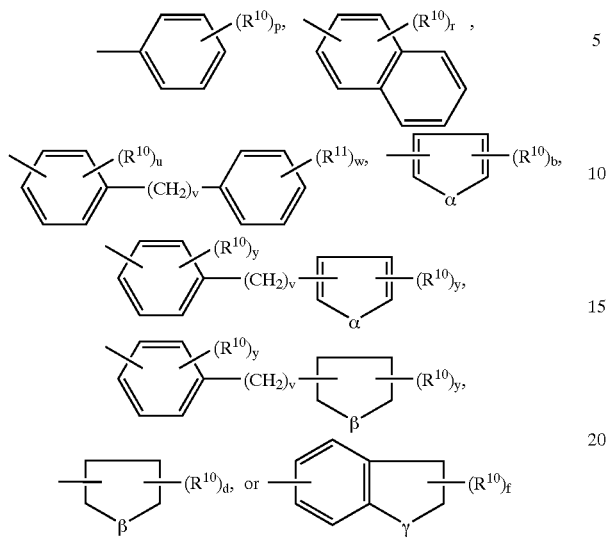

wherein v is an integer from 0 to 2; $R^{10}$ and $R^{11}$ are each independently selected from a halogen, C1 to C10 alkyl, C1 to C10 alkyloxy, C1 to C10 alkylthio, optionally substituted phenyl, and C1 to C10 haloalkyl, α is an oxygen atom or a sulfur atom, β is —$CH_2$— or —$(CH_2)_2$—; γ is an oxygen atom or a sulfur atom; b is an integer from 0 to 3, d is an integer from 0 to 4; f, p, and w are an integer from 0 to 5; r is an integer from 0 to 7, and u is an integer from 0 to 4. When the above b, d, f, p, r, u, and/or w are 2 or more, a plural number of $R^{10}$ or $R^{11}$ may be different from one another. When $R^{10}$ is a substituent on the naphthyl group, the substituent may be substituted at any arbitrary position on the naphthyl group. —$CH_2$— and —$(CH_2)_2$— in β may be substituted with $R^{10}$.

A more preferable example includes (h) a group represented by the formula:

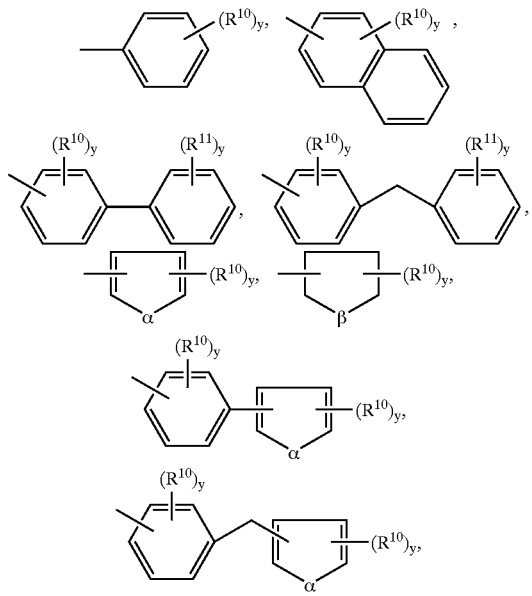

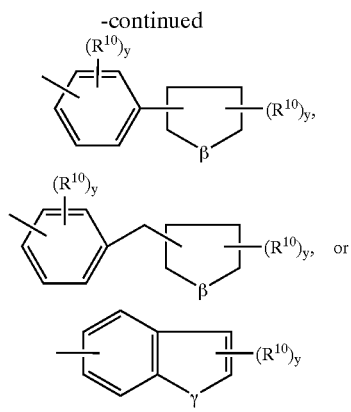

wherein $R^{10}$, $R^{11}$, α, β, and γ are the same as defined above, and y is independently 0 or 1. When $R^{10}$ is a substituent on the naphthyl group, the substituent may be substituted at any arbitrary position on the naphthyl group. —$CH_2$— and —$(CH_2)_2$— in β may be substituted with $R^{10}$.

The term "non-interfering substituent" in the present specification means a group suitable for substitution of group (a) (e.g., "alkyl", "alkenyl" "carbocyclic group" and "heterocyclic group") in $R^1$ on tricyclic compound represented by the formula (I). An example of the non-interfering substituents includes C1 to C10 alkyl, C2 to C6 alkenyl, C2 to C6 alkynyl, C7 to C12 aralkyl (such as benzyl and phenethyl), C7 to C12 alkaryl, C3 to C8 cycloalkyl, C3 to C8 cycloalkenyl, phenyl, tolyl, xylyl, biphenylyl, C1 to C10 alkyloxy, C1 to C6 alkyloxy C1 to C6 alkyl (such as methyloxymethyl, ethyloxymethyl, methyloxyethyl, and ethyloxyethyl), C1 to C6 alkyloxy C1 to C6 alkyloxy (such as methyloxymethyloxy and methyloxyethyloxy), C1 to C6 alkylcarbonyl (such as methylcarbonyl and ethylcarbonyl), C1 to C6 alkylcarbonylamino (such as methylcarbonylamino and ethylcarbonylamino), C1 to C6 alkyloxyamino (such as methyloxyamino and ethyloxyamino), C1 to C6 alkyloxyaminocarbonyl (such as methyloxyaminocarbonyl and ethyloxyaminocarbonyl), mono or di C1 to C6 alkylamino (such as methylamino, ethylamino, dimethylamino, and ethylmethylamino), C1 to C10 alkylthio, C1 to C6 alkylthiocarbonyl (such as methylthiocarbonyl and ethylthiocarbonyl), C1 to C6 alkylsulfinyl (such as methylsulfinyl and ethylsulfinyl), C1 to C6 alkylsulfonyl (such as methylsulfonyl and ethylsulfonyl), C2 to C6 haloalkyloxy (such as 2-chloroethyloxy and 2-bromoethyloxy), C1 to C6 haloalkylsulfonyl (such as chloromethylsulfonyl and bromomethylsulfonyl), C1 to C10 haloalkyl, C1 to C6 hydroxyalkyl (such as hydroxymethyl and hydroxyethyl), C1–C6 alkyloxycarbonyl (such as methyloxycarbonyl and ethyloxycarbonyl), —$(CH_2)_z$—O—(C1 to C6 alkyl), benzyloxy, aryloxy (such as phenyloxy), arylthio (such as phenylthio), —$CONHSO_2R^{20}$, formyl, amino, amidino, halogen, carbamyl, carboxyl, carbalkyloxy, —$(CH_2)_z$—COOH (such as carboxymethyl, carboxyethyl, and carboxypropyl), cyano, cyanoguanidino, guanidino, hydrazido, hydrazino, hydroxy, hydroxyamino, nitro, phosphono, —$SO_3H$, thioacetal, thiocarbonyl, carbocyclic groups, heterocyclic groups and the like, wherein z is an integer from 1 to 8 and $R^{20}$ is C1 to C6 alkyl or aryl. Preferable are halogens, C1 to C6 alkyl, C1 to C6 alkyloxy, C1 to C6 alkylthio, and C1 to C6 haloalkyl as the "non-interfering substituent" in the $R^1$. More preferable are halogens, C1 to C3 alkyl, C1 to C3 alkyloxy, C1 to C3 alkylthio, and C1 to C3 haloalkyl.

The term "halogen" in the present specification means fluorine, chlorine, bromine, and iodine.

The term "cycloalkyl" in the present specification means a monovalent cyclic hydrocarbon group having a specified number of carbon atoms. An example of the cycloalkyl includes cyclopropyl, cyclobutyl, cyclopentyl, cyclohexyl, cycloheptyl, cyclooctyl and the like.

The term "cycloalkenyl" in the present specification means a monovalent cyclic hydrocarbon group having a specified number of carbon atoms and at least one double bond(s). An example of the cycloalkenyl includes 1-cyclopropenyl, 2-cyclopropenyl, 1-cyclobutenyl, 2-cyclobutenyl and the like.

In the present specification, an example of "alkyloxy" includes methyloxy, ethyloxy, n-propyloxy, isopropyloxy, n-butyloxy, n-pentyloxy, n-hexyloxy and the like.

In the present specification, an example of "alkylthio" includes methylthio, ethylthio, n-propylthio, isopropylthio, n-butylthio, n-pentylthio, n-hexylthio and the like.

The term "acidic group" in the present specification means an organic group functioning as a proton donor capable of hydrogen bonding when attached to a tricyclic nucleus through a suitable linking atom (hereinafter defined as "acid linker"). An example of the acidic group includes (k) a group represented by the formula:

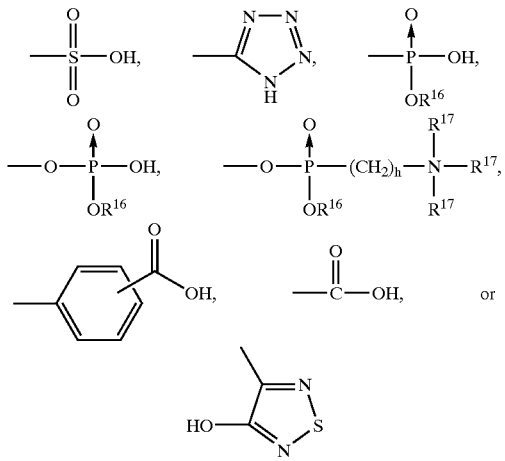

wherein $R^{16}$ is a hydrogen atom, a metal, or C1 to C10 alkyl; each $R^{17}$ is independently a hydrogen atom or C1 to C10 alkyl; h is an integer from 1 to 8. Preferable is (l) —COOH, —SO$_3$H, or P(O)(OH)$_2$. More preferable is (m) —COOH. And preferable is also their ester and prodrug.

The term "acid linker" in the present specification means a divalent linking group represented by a symbol —(L$^2$)—, and it functions to join tricyclic nucleus to an "acidic group" in the general relationship. An example of it includes (n) a group represented by the formula:

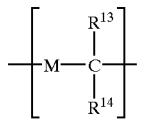

wherein M is —CH$_2$—, —O—, —(N$^{15}$)—, or —S—, and $R^{13}$ and $R^{14}$ are each independently a hydrogen atom, C1 to C10 alkyl, aryl, aralkyl, carboxy, or halogens, wherein $R^{15}$ is a hydrogen atom or C1–C6 alkyl. Preferable are (o) —O—CH$_2$—, —S—CH$_2$—, —N(R$^{15}$)—CH$_2$—, —CH$_2$—CH$_2$—, —O—CH(CH$_3$)—, or —O—CH((CH$_2$)$_2$Ph)— wherein $R^{15}$ is a hydrogen atom, C1 to C6 alkyl and Ph is phenyl. More preferable is (p) —O—CH$_2$—, —O—CH(CH$_3$)—, or —S—CH$_2$—.

In the present specification, the term "acid linker length" means the number of atoms (except for hydrogen atoms) in the shortest chain of a linking group —(L$^2$)— which connects tricyclic nucleus with the "acidic group". The presence of a carbocyclic ring in —(L$^2$)— counts as the number of atoms approximately equivalent to the calculated diameter of the carbocyclic ring. Thus, a benzene and cyclohexane ring in the acid linker counts as two atoms in culculating the length of —(L$^2$)—. A preferable length is 2 to 3.

The term "haloalkyl" in the present specification means the aforementioned "alkyl" substituted with the aforementioned "halogen" at arbitrary position(s). An example of the haloalkyl includes chloromethyl, trifluoromethyl, 2-chloromethyl, 2-bromomethyl and the like.

The term "hydroxyalkyl" in the present specification means the aforementioned "alkyl" substituted with hydroxy at arbitrary position(s). An example of the hydroxyalkyl includes hydroxymethyl, 2-hydroxyethyl, 3-hydroxypropyl and the like. In this case, hydroxymethyl is preferable.

In the present specification, the term "haloalkyl" in "haloalkyloxy" is the same as defined above. An example of it includes 2-chloroethyloxy, 2-trifluoroethyloxy, 2-chloroethyloxy and the like.

The term "aryl" in the present specification means a monocyclic or condensed cyclic aromatic hydrocarbon. An example of the aryl includes phenyl, 1-naphthyl, 2-naphthyl, anthryl and the like. Particularly, phenyl and 1-naphthyl are preferred.

The term "aralkyl" in the present specification means a group wherein C1 to C8 alkyl is substituted with the above-mentioned "aryl". Such aryl may have a bond at any substitutable position. An example of it includes benzyl, phenethyl, phenylpropyl (such as 3-phenylpropyl), naphthylmethyl (such as 1-naphthylmethyl) and the like.

The term "alkyloxycarbonyl" in the present specification means C1–C6 alkyloxycarbonyl. An example of the alkyloxycarbonyl includes methyloxycarbonyl, ethyloxycarbonyl, n-propyloxycarbonyl and the like.

The term "acyl" in the present specification means C1–C6 alkylcarbonyl or arylcarbonyl opptionally substituted with a halogen and the like. An example of the acyl includes acetyl, trifluoroacetyl, propionyl, benzoyl and the like.

A group of preferable substituents as the $R^1$ to $R^3$ of the compound represented by the formula (I) will be shown in items (A) to (O). Preferable are hydrogen atoms as the $R^4$, $R^{18}$, $R^{19}$, $R^{20}$, $R^{21}$, $R^{22}$, $R^{23}$, $R^{25}$, $R^{26}$, and $R^{27}$. Item (f) to (p) are the same groups as described above.

As the $R^1$, (A):—(L$^1$)—R$^5$, (B):—(CH$_2$)$_{1-2}$-(f), (C):—(CH$_2$)$_{1-2}$-(g), (D):—(CH$_2$)$_{1-2}$-(h) are preferred.

As the $R^2$, (E): CONH$_2$ or CONHNH$_2$, and (F): CONH$_2$ are preferred.

As the $R^3$, (G):-(n)-(k), (H):-(n)-(l), (I):-(n)-(m), (J):-(o)-(k), (K):-(o)-(l), (L):-(o)-(m), (M):-(p)-(k), (N):-(p)-(l), and (O):-(p)-(m) are preferred.

A preferred group of compounds represented by the formula (I) is shown below.

($R^1,R^2,R^3$)=(A,E,G), (A,E,H), (A,E,I), (A,E,J), (A,E,K), (A,E,L), (A,E,M), (A,E,N), (A,E,O), (A,F,G), (A,F,H), (A,F,I), (A,F,J), (A,F,K), (A,F,L), (A,F,M), (A,F,N), (A,F,O), (B,E,G), (B,E,H), (B,E,I), (B,E,J), (B,E,K), (B,E,L), (B,E,M), (B,E,N), (B,E,O), (B,F,G), (B,F,H), (B,F,I), (B,F,J), (B,F,K), (B,F,L), ((B,F,M), (B,F,N), (B,F,O), (C,E,G), (C,E,H), (C,E,I), (C,E,J), (C,E,K), (C,E,L), (C,E,M), (C,E,N), (C,E,O), (C,F,G), (C,F,H), (C,F,I), (C,F,J), (C,F,K), (C,F,L), (C,F,M), (C,F,N), (C,F,O), (D,E,G), (D,E,H), (D,E,I), (D,E,J), (D,E,K), (D,E,L), (D,E,M), (D,E,N), (D,E,O), (D,F,G), (D,F,H), (D,F,I), (D,F,J), (D,F,K), (D,F,L), (D,F,M), (D,F,N), and (D,F,O).

For each group as the $R^4$, a hydrogen atom, C1 to C3 alkyl and aryl are preferable.

BEST MODE FOR CARRYING OUT THE INVENTION

The compounds of the invention represented by the formula (I) can be synthesized in accordance with well-known method described in chemical journals. The compounds of the invention represented by the formula (I) can also be synthesized in accordance with the following methods A and method B. Although representative methods are exemplified, enlarged rings can also be synthesized in a similar manner.

(Method A)

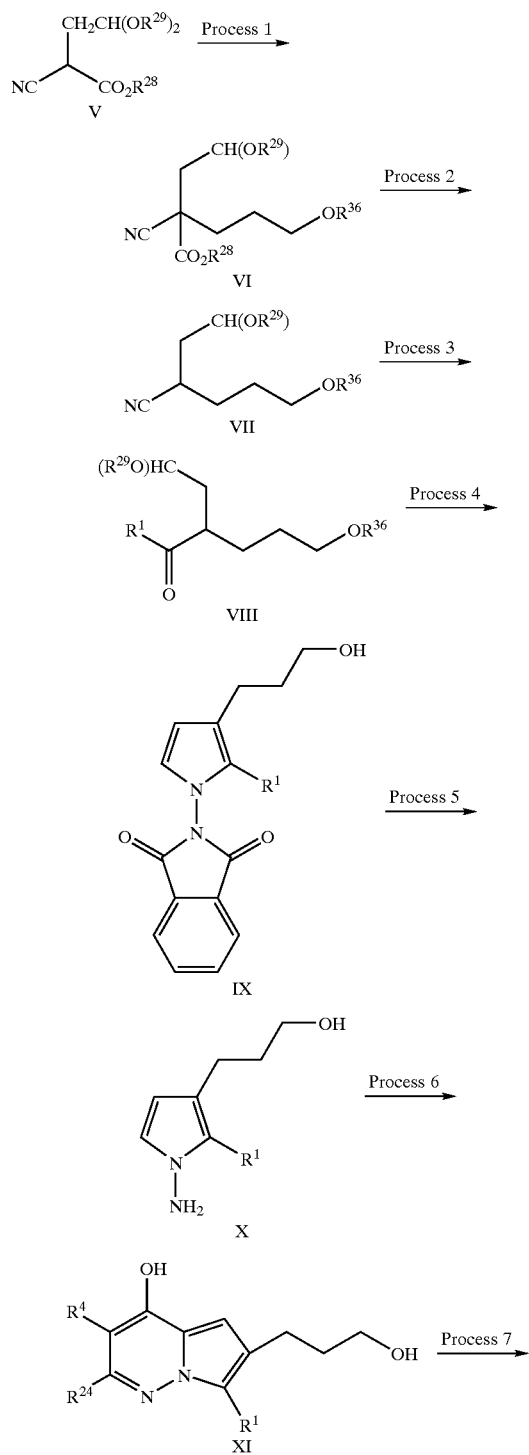

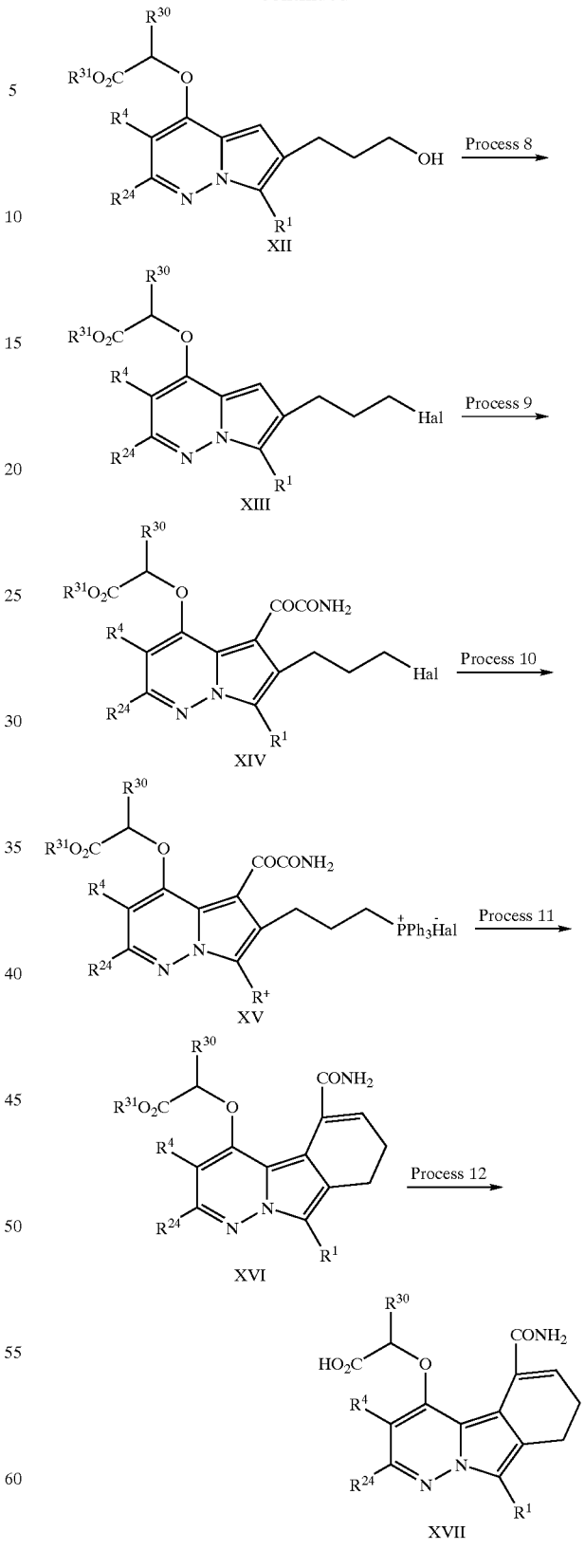

wherein $R^1$, $R^4$, and $R^{24}$ are as defined above, $R^{28}$, $R^{29}$ and $R^{31}$ is C1 to C3 alkyl, $R^{36}$ is a protecting group of hydroxy (e.g., tetrahydropyranyl or the like), $R^{30}$ is a hydrogen atom or C1 to C3 alkyl, Hal are each independently a halogen.
(Process 1)
To a solution of the compound (V) in a solvent such as dimethylformamide or the like are added an alkyl halide derivative and a base (e.g. potassium carbonate, potassium t-butoxide, sodium hydride or the like), and the mixture is reacted at room temperaturre to 180° C., preferably 20 to 150° C. for 3 to 80 h, preferably 5 to 70 h to give the compound (VI).
(Process 2)
To a solution of the compound (VI) in a solvent such as dimethylsulfoxide or the like is added a reagent such as potassium acetate, sodium acetate or the like, and the mixture is reacted at 20° C. to 200° C., preferably 100° C. to 180° C. for 3 to 17 h to obtain the compound (VII).
(Process 3)
To a solution of a Grignard reagent ($R^1$MgHal, Hal is a halogen) or $R^1$Li in a solvent such as ether, tetrahydrofuran, or dimethoxyethane is added a solution of the compound (VII) in a solvent such as ether, tetrahydrofuran, or dimethoxyethane at −20° C. to 30° C., and the mixture is reacted at 0° C. to 70° C., preferably 20 C to 60° C. for 1 to 48 h, preferably 2 to 24 h to obtain the compound (VIII).
(Process 4)
To a solution of the compound (VIII) in a solvent such as ethanol, methanol, dioxane, tetrahydrofuran or the like are added N-aminophthalimide and an acid such as trifluoroacetic acid, hydrochloric acid, sulfuric acid or the like, and the mixture is reacted at 20° C. to 120° C., preferably 50° C. to 100° C. for 6 min to 2 h, preferably 10 min to 1 h to yield the compound (IX).
(Process 5)
The present process includes the deprotection of a phthalimide group of the compound (IX). This can be carried out by usual deprotection (to see Protective Groups in Organic Synthesis, Theodora W Green (John Wilkey & Sons)). For example, to a solution of the compound (IX) in an alcoholic solvent such as ethanol or the like is added hydrazine, and the mixture is reacted at 50° C. to 100° C., for 0.5 to 3 h to yield the amino compound (X).
(Process 6)
To a solution of the compound (X) in a solvent such as chloroform, dichloroethane, tetrahydrofuran, toluene or the like are added β-ketoester (e.g., acetoacetic acid methyl ester) and an acid catalyst (e.g., p-toluenesulfonic acid, methanesulfonic acid, hydrochloric acid, sulfuric acid, trifluoroacetic acid or the like), and the mixture is reacted at 20° C. to 150° C., preferably 30° C. to 100° C. for 1 to 20 h, preferably 3 to 16 h to yield the compound (XI). Water which is yielded in the reaction is dehydrated with a Dean-stark filled with molecular sieves 4A.
(Process 7)
To a solution of the compound (XI) in a solvent such as tetrahydrofuran, dimethylformamide or the like are added a base such as potassium carbonate, sodium hydride or the like and an alkyl halide derivative, and the mixture is reacted at 0° C. to 100° C., preferably 20 to 40° C. for 1 to 15 h to obtain the compound (XII).
(Process 8)
The present process includes the conversion of a hydroxy group to a halogen. To a solution of the compound (XII) in a solvent such as dichloromethane or the like are added reagents such as triphenylphosphine and carbon tetrachloride, N-bromosuccimide or the like, and the mixture is reacted at 0° C. to 50° C., preferably 0° C. to 30° C. for 1 to 10 h, preferably for 1 to 5 h to obtain the compound (XIII).

(Process 9)
The present process includes the introduction of a substituent at 5-position. To a solution of the compound (XIII) in a solvent such as dichloromethane or tetrahydrofuran are added Hal—C(=X)—C(=X)—Hal (Hal are halogen) (e.g., oxalyl chloride) and a base such as N-methylmorpholine, triethylamine or the like, and the mixture is stirred at −20° C. to 70° C., preferably −20° C. to 40° C. for 10 min to 10 h, preferably, 10 min to 2 h. The reaction mixture is poured into a cold aqueous ammonium and the resulting reaction mixture is subjected to a usual work-up, and then the compound (XIV) can be obtained.
(Process 10)
The present process includes the preparation of the phosphonium salt. A mixture of the compound (XIV) and triphenylphosphine in a solvent such as acetonitrile, toluene or the like is reacted at 60° C. to 150° C., preferably 80° C. to 120° C. for 5 to 100 h, preferably 10 to 70 h to obtain the compound (XV).
(Process 11)
The present process is the one for constructing a ring by Wittig reaction. To a solution of the compound (XV) in a solvent such as dichloromethane, acetonitrile, tetrahydrofuran or the like is added a base such as 1,8-dizabicyclo[6.4.0]-7-undecene (DBU), potassium t-butoxide or the like, and the mixture is reacted at 20° C. to 120° C., preferably 30° C. to 100° C. for 3 to 24 h, preferably 5 to 10 h to obtain the compound (XVI).
(Process 12)
The present process includes hydrolysis. To a solution of the compound (XVI) in a solvent such as methanol, tetrahydrofuran or the like is added a base such as sodium hydroxide or the like, and the mixture is reacted at 0° C. to 40° C., preferably 10° C. to 30° C. for 0.5 to 6 h, preferably for 0.5 to 2 h, to obtain the compound (XVII).
(Method B)

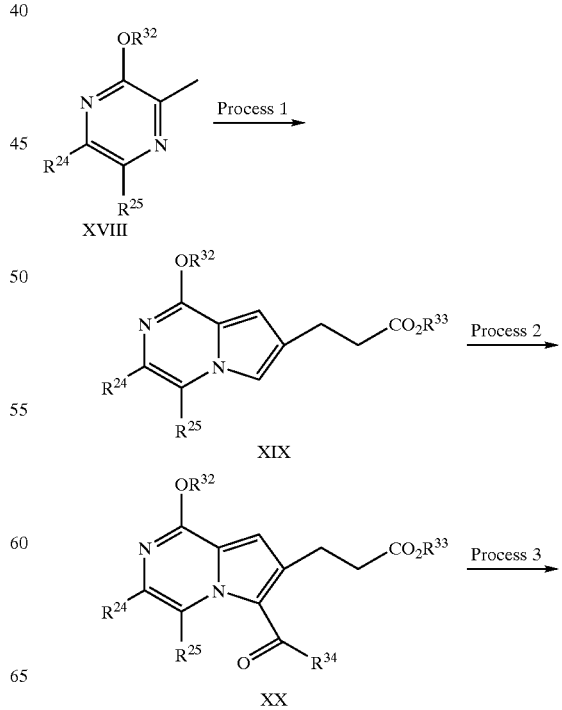

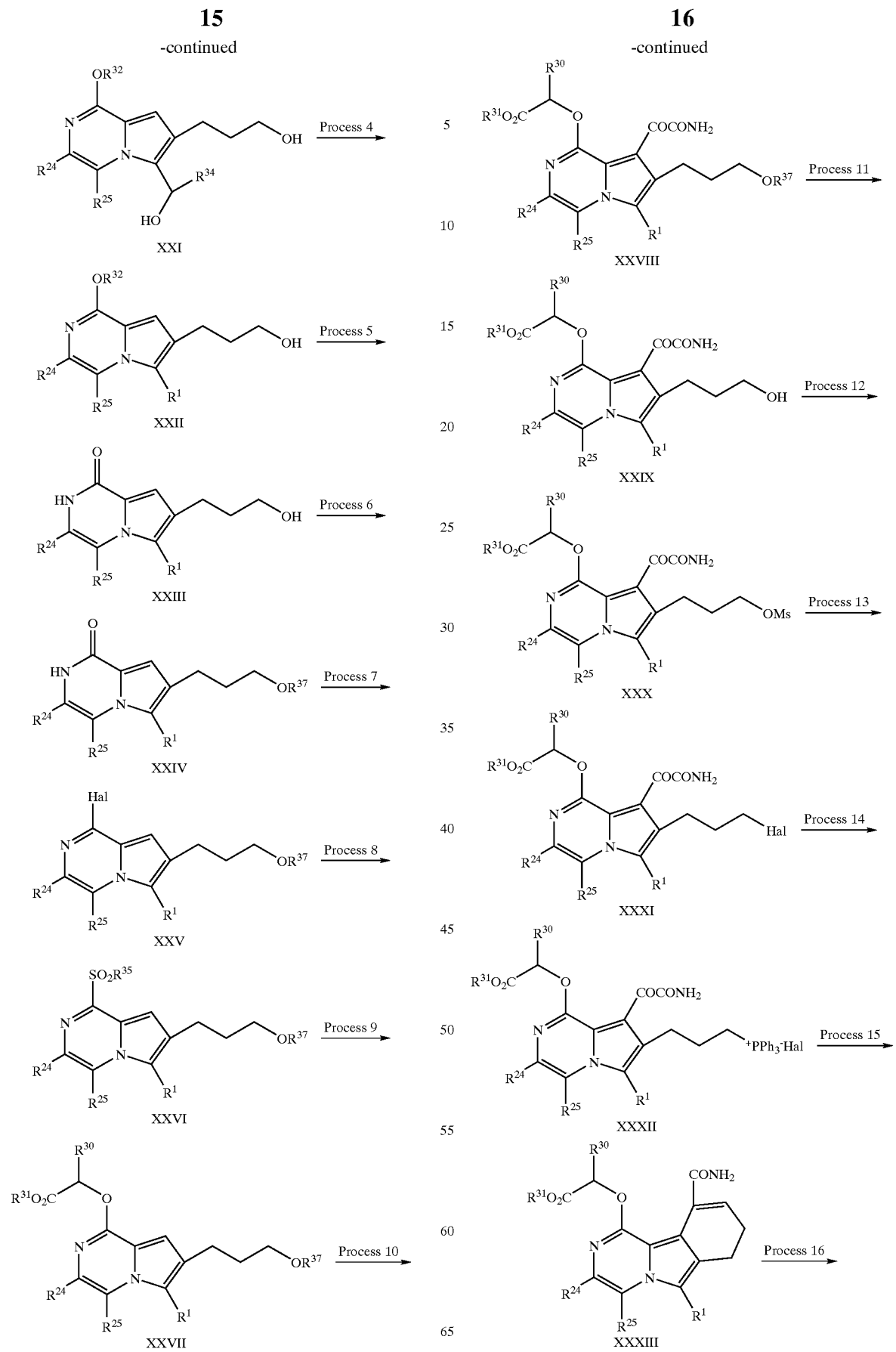

-continued

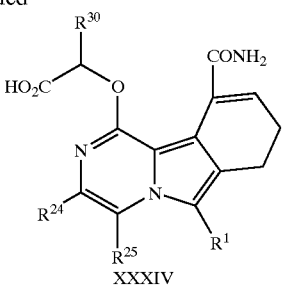

XXXIV wherein $R^1$, $R^{24}$, $R^{25}$, $R^{30}$, $R^{31}$, and Hal are defined above. $R^{32}$ and $R^{33}$ C1 to C3 alkyl, $R^{34}$ is a precursor of $R^1$, $R^{35}$ C1–C3 alkyl, optionally substituted aryl (e.g., tolyl or the like), $R^{37}$ is acyl (e.g., acetyl, benzoyl or the like), Ms mesyl;

(Process 1)

The present process is the one for constructing pyrrolo [1,2-a]pyrazine ring. A mixture of the compound (XVIII) and Hal—$CH_2$—C(=O)—$CH_2$—$(CH_2)_m$—$CO_2R^{33}$ is stirred at 40° C. to 90° C., preferably 50° C. to 70° C. for 3 to 36 preferably 12 to 24 h, to obtain a quaternary salt. The resulting quaternary salt is dissolved in a solvent such as 1,2-dichloroethane, acetonitrile or the like, a base such as 1,8-diazabicyclo[5,4,0]-undec-7-ene (DBU), triethylamine or the like is added to the solution, and the mixture is stirred at 40° C. to 90° C., preferably 60° C. to 80° C. for 1 to 10 hours, preferably 1 to 5 h. When the resulting product is subjected to a usual work-up, the compound (XIX) can be obtained.

(Process 2)

The present process is the one for introducing a substituent to 6-position of pyrrolo[1,2-a]pyrazine, and it may be carried out by Friedel-Crafts reaction. The compound (XIX) is dissolved in a solvent such as dichloromethane, chlorobenzene or the like, $R^{34}$COHal and Lewis acid (e.g., $AlCl_3$, $SbF_5$, $BF_3$ and the like) are added gradually to the solution at −78° C. to 10° C., preferably −20° C. to 0° C., and the resulting mixture is stirred at −10° C. to 10° C., preferably 0° C. to 10° C. for 30 min to 5 h, preferably 1 h to 3 h. When the resulting product is subjected to a usual work-up, the compound (XX) can be obtained.

(Process 3)

The present process is the one for reduction of the ester group and the ketone group to the alcohol groups. To a solution of the compound (XX) in a solvent such as ether, tetrahydrofuran or the like is reacted with a reductant such as lithium aluminum hydride, lithium borohydride or the like at 0° C. to 80° C., preferably 10° C. to 40° C. for 30 min to 10 h, preferably for 1 h to 5 h, to obtain the compound (XXI).

(Process 4)

The present process is the one for reductive elimination of the hydroxy group and transformation the same into methylene. Lewis acid (for example, $AlCl_3$ and the like) is dissolved in a solvent such as dichloromethane, tetrahydrofuran or the like, a reducing agent such as boron-t-butylamine complex, sodium borohydride or the like is added to the solution at −20° C. to 10° C., preferably under ice-cooling, and the resulting mixture is stirred for 5 to 30 minutes, preferably 10 to 20 minutes. The compound (XXI) is added to the reaction mixture at −20° C. to 10° C., preferably under ice-cooling, the resulting mixture is reacted at 15° C. to 40° C., preferably 20° C. to 30° C. for 30 min to 5 h, preferably 1 to 3 h to obtain the compound (XXII).

(Process 5)

The present process is the one for transforming the alkyloxy group into ketone. An acid such as concentrated hydrochloric acid or the like is added to the compound (XXII), and the mixture is stirred at 80° C. to 150° C., preferably 100° C. to 120° C. for 1 to 5 h, preferably 1 to 3 h. When the resulting product is subjected to a usual work-up, the compound (XXIII) can be obtained.

(Process 6)

The present process is the one for protecting the hydroxy group with a acetyl group. A solution of the compound (XXIII) in pyridine is reacted with acetic anhydride at 0° C. to 50° C., preferably 20° C. to 40° C. for 1 to 10 h, preferably 3 to 8 h to give the compound (XXIV).

(Process 7)

The present process is the one for transforming the ketone at 1-position into a halogen. A halogenating agent such as phosphorus oxychloride, phenylphosphonic dichloride or the like is added to the compound (XXIV), and the mixture is stirred at 60° C. to 150° C., preferably 80° C. to 110° C. for 10 min to 3 h, preferably 30 min to 1 h. When the resulting product is subjected to an ordinary work-up, the compound (XXV) can be obtained.

(Process 8)

The present process is the one for converting the halogen at 1-position into a sulfonyl group. To a solution of the compound (XXV) in ethanol is added $R^{36}SO_2Na$, and the mixture is refluxed for 10 to 50 h, preferably 24 to 36 h to obtain the compound (XXVI).

(Process 9)

The present process is the one for transforming the sulfonyl group at 1-position into an alkyloxy group. A suspension of $HOCH(R^{30})CO_2R^{31}$ and a reagent such as sodium hydride, potassium t-butoxide or the like in a solvent such as tetrahydrofuran or the like is stirred at −20° C. to 50° C., preferably 0° C. to 30° C. for 15 min to 2 h, preferably 30 min to 1 h. To the mixture is added the compound (XXVI), and the reaction mixture is reacted at −20° C. to 50° C., preferably 0° C. to 30° C. for 15 min to 5 h, preferably 30 min to 2 h to yield the compound (XXVII).

(Process 10)

The present process may be carried out in accordance with the same manner as that of the method A—process 9.

(Process 11)

The present process is the one for deprotecting the acetyl group. To a solution of the compound (XXVIII) in a solvent mixed with tetrahydrofuran and methanol is added hydrochloric acid and the mixture is stirred at 0° C. to 50° C., preferably 20° C. to 30° C. for 1 to 10 h, preferably 3 to 8 h to obtain the compound (XXIX).

(Process 12)

The present process is the one for converting the hydroxy group into —$OSO_2Me$. A solution of the compound (XXIX) in a solvent such as dichloromethane, tetrahydrofuran or the like is reacted in the presence of a base such as triethylamine, pyridine or the like with methanesulfonyl chloride at −20° C. to 50° C., preferably 0° C. to 30° C. for 10 min to 5 h, preferably 30 min to 2 h to obtain the compound (XXX).

(Process 13)

The present process is the one for transformation of the —$OSO_2Me$ group into a halogen. A solution of the compound (XXX) in a solvent such as acetonitrile, acetone, dimethylformamide or the like is reacted with a reagent such as lithium bromide, lithium chloride or the like at 0° C. to 100° C., preferably 30° C. to 60° C. for 1 to 10 h, preferably 1 to 5 h to obtain the compound (XXXI).

(Process 14)

The present process may be carried out in accordance with the same manner as that of the method A—process 10.

(Process 15)

The present process may be carried out in accordance with the same manner as that of the method A—process 11.

(Process 16)

The present process may be carried out in accordance with the same manner as that of the method A—process 12.

Where a compound of the present invention has an acidic or basic functional group, a variety of salts having higher water solubility and more physiologically suitable properties than those of the original compound can be formed. An example of typical pharmaceutically acceptable salts includes salts with alkali metal and alkaline earth metal such as lithium, sodium, potassium, calcium, magnesium, aluminum and the like, but it is to be noted that such pharmaceutically acceptable salts are not limited thereto. A salt is easily manufactured from a free acid by either treating an acid in a solution with a base, or allowing an acid to be in contact with an ion exchange resin. Additional salts of the compounds according to the present invention with relatively non-toxic inorganic bases and organic bases, for example, amine cation, ammonium, and quaternary ammonium derived from nitrogenous bases having a basicity sufficient for forming a salt of the compounds of the present invention are included in the definition of "pharmaceutically acceptable salts". (e.g., S. M. Berge et al., "Pharmaceutical Salts," J. Phar. Sci., 66, 1–19 (1977)) Furthermore, basic groups of a compound according to the present invention are reacted with a suitable organic or inorganic acid to form salts such as acetates, benzenesulfonates, benzoates, bicarbonates, bisulfates, bitartarate, borates, bromides, camcyrates, carbonates, chlorides, clubranates, citrates, edetates, edicirates, estrates, ethylates, fluorides, fumarates, gluseptates, gluconates, glutamates, glycolialsanyrates, hexylresorcinates, hydroxynaphthoates, iodides, isothionates, lactates, lactobionates, laurates, malates, malseates, manderates, mesylates, methylbromides, methylnitrates, methylsulfates, mucates, napcylates, nitrates, oleates, oxarates, palmitates, pantothenates, phosphates, polygalacturonates, salicirates, stearates, subacetates, sucinates, tanates, tartrates, tosylates, trifluoroacetates, trifluoromethanesulfonates, valerates and the like. In case of forming a hydrate, a questioned compound may be coordinated with a suitable number of water molecules.

In the case where a compound of the present invention has one or more of chiral center(s), it may exist as an optically active member. Likewise, in the case where a compound contains alkenyl or alkenylene, there is a possibility of cis- and trans-isomers. Mixtures of R- and S-isomers as well as of cis- and trans-isomers, and mixtures of R- and S-isomers containing racemic mixture are included in the scope of the present invention. Asymmetric carbon atom may exist also in a substituent such as alkyl group. All such isomers are included in the present invention together with these mixtures. In the case where a specified streoisomer is desired, either it is manufactured by applying a manner which has been well known by those skilled in the art wherein a starting material having an asymmetrical center which has been previously separated is subjected to stereospecific reaction to the starting material, or it is manufactured by preparing a mixture of stereoiromers, and thereafter separating the mixture in accordance with a well-known manner.

Prodrug is a derivative of the compound having a group which can be decomposed chemically or metabolically, and such prodrug is a compound according to the present invention which becomes pharmaceutically active by means of solvolysis or by placing the compound in vivo under a physiological condition. Although a derivative of the compounds according to the present invention exhibits activity in both forms of acid derivative and basic derivative, acid derivative is more advantageous in solubility, tissue affinity, and release control in mammal organism (Bungard, H., Design of Prodrugs, pp. 7–9, 21–24, Elsevier, Amsterdam, 1985). For instance, prodrugs each containing an acid derivative such as an ester which is prepared by reacting a basal acid compound with a suitable alcohol, or an amide which is prepared by reacting a basal acid compound with a suitable amine are well known by those skilled in the art. Simple aliphatic or aromatic esters derived from acid groups contained in the compounds according to the present invention are preferable prodrugs. More preferable is C1–C6 alkyl ester of acidic group (e.g., methyl ester, ethyl ester). Double ester such as (acyloxy)alkyl ester or ((alkyloxycarbonyl)oxy)alkyl ester type prodrugs may be optionally manufactured.

The term "inhibit" means that release of fatty acid started by sPLA$_2$ decreases significantly by the compounds of the present invention from viewpoint of prevention and treatment of disease. The term "pharmaceutically acceptable" means that carriers, diluents, or additives are compatible with other ingredients in a formulation and are not harmful for recipients.

The compounds of the present invention exhibit sPLA$_2$ inhibiting activity as per the description of the experimental examples which will be described hereinafter. Accordingly, when a curatively effective amount of the compounds represented by the formulae (I), (II), and (III), the prodrug derivatives thereof, or their pharmaceutically acceptable salts, or their hydrate is administered to any of mammals (including human being), it functions effectively as a curative medicine for diseases of septic shock, adult respiratory distress syndrome, pancreatitis, injury, bronchial asthma, allergic rhinitis, chronic rheumatism, arterial sclerosis, cerebral hemorrhage, cerebral. infarction, inflammatory colitis, psoriasis, cardiac failure, cardiac infarction.

The compounds of the present invention may be administered to a patient through a variety of routes including oral, aerosol, rectal, percutaneous, subcutaneous, intravenous, intramuscular, and nasal routes. A formulation according to the present invention may be manufactured by combining (for example, admixing) a curatively effective amount of a compound of the present invention with a pharmaceutically acceptable carrier or diluent. The formulation of the present invention may be manufactured with the use of well-known and easily available ingredients in accordance with a known method.

In case of manufacturing a composition according to the present invention, either active ingredients are admixed with a carrier, or they are diluted with a carrier, or they are contained in a carrier in the form of capsule, sacheier, paper, or another container. In case of functioning a carrier as a diluent, the carrier is a solid, semi-solid, or liquid material which functions as a medium. Accordingly, a formulation according to the present invention may be produced in the form of tablet, pill, powder medicine, intraoral medicine, elixir agent, suspending agent, emulsifier, dissolving agent, syrup agent, aerosol agent (solid in liquid medium), and ointment. Such a formulation may contain up to 10% of an active compound. It is preferred to prepare a compound according to the present invention prior to administration.

Any suitable carrier which has been well known by those skilled in the art may be used for the formulation. In such formulation, a carrier is in the form of solid, liquid, or a mixture of solid and liquid. For instance, a compound of the present invention is dissolved into 4% dextrose/0.5% sodium citrate aqueous solution so as to be 2 mg/ml concentration for intravenous injection. Solid formulation includes powder, tablet, and capsule. Solid carrier consists of one or more of material(s) for serving also as fragrant, lubricant, dissolving agent, suspension, binder, tablet disintegrator, capsule. A tablet for oral administration contains a suitable excipient such as calcium carbonate, sodium carbonate, lactose, calcium phosphate and the like together with a disintegrator such as corn starch, alginic acid and the like and/or a binder such as gelatin, acacia and the like, and a lubricant such as magnesium stearate, stearic acid, talc and the like.

In a powder medicine, a carrier is a finely pulverized solid which is blended with finely pulverized active ingredients. In a tablet, active ingredients are admixed with a carrier having required binding power in a suitable ratio, and it is solidified in a desired shape and size. Powder medicine and tablet contain about 1 to about 99% by weight of the active ingredients being novel compounds according to the present invention. An example of suitable solid carriers includes magnesium carbonate, magnesium stearate, talc, sugar, lactose, pectin, dextrin, starch, gelatin, tragacanth gum, methyl cellulose, sodium carboxymethylcellulose, low-melting wax, and cocoa butter.

An axenic liquid formulation contains suspending agent, emulsifier, syrup agent, and elixir agent. Active ingredients may be dissolved or suspended into a pharmaceutically acceptable carrier such as sterile water, a sterile organic solvent, a mixture thereof and the like. Active ingredients may be dissolved frequently into a suitable organic solvent such as propylene glycol aqueous solution. When finely pulverized active ingredients are dispersed into aqueous starch, sodium carboxylmethylcellulose solution, or suitable oil, the other compositions can be prepared.

The dosage varies with the conditions of the disease, administration route, age and body weight of patient. In the case of oral administration, the dosage can generally be between 0.01 to 50 mg/kg/day for adult.

The following examples are provided to further illustrate the present invention and are not to be constructed as limiting the scope thereof.

Abbreviations described below are used in the following examples.

Me: methyl
Et: ethyl
Hex: hexyl
Ph: phenyl
Bn: benzyl
Tol: tolyl
Ac: acetyl
Ms: mesyl
DBU: 1,8-diazabicyclo[5.4.0]-7-undecene

EXAMPLE

Example 1

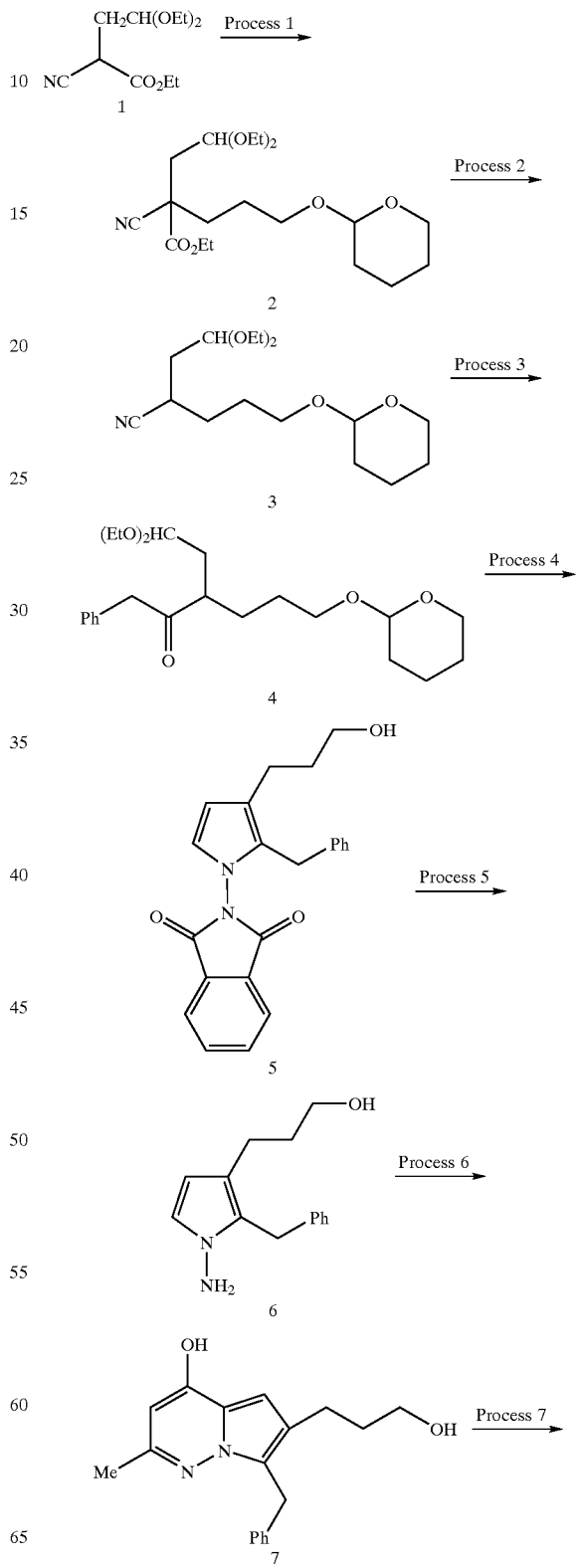

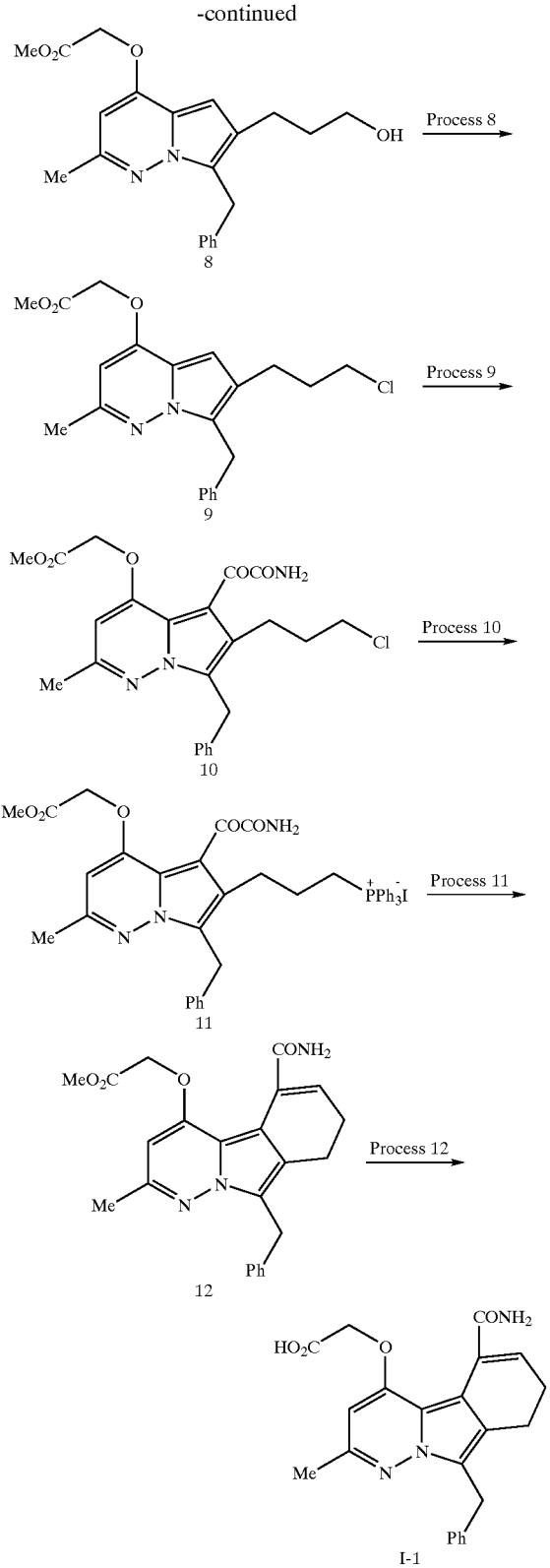

(Process 1)

The compound (1) (30.0 g, 0.313 mol) was added to a suspension of sodium hydride (3.77 g, 0.617 mol) in dimethylformamide (100 ml) under nitrogen atmosphere below 20° C., and the mixture was stirred at room temperature for 30 min. To the resulting mixture was added 2-(3-chloropropyl)tetrahydro-2H-pyran (25.7 g, 0.144 mol) at the same temperature, then the mixture was stirred in an oil bath at 60° C. for 16 h. The reaction mixture is evaporated under reduced pressure to remove dimethylformamide, to the residue was added water and the mixture was extracted with toluene. After the toluene layer was washed with water, dried over magnesium sulfate, and evaporated to remove toluene, the excess of 2-(3-chloropropyl)tetrahydro-2H-pyran was distilled and removed in an oil bath at 150° C. under reduced pressure to give the compound (2) (41.5 g, 85.4%).

$^1$H NMR (CDCl$_3$); 1.18 (3H, t, J=6.9 Hz), 1.21 (3H, t, J=6.9 Hz), 1.33 (3H, t, J=7.2 Hz), 1.52–2.04 (12H, m), 2.40 (1H, m), 3.39–3.86 (7H, m), 4.24 (2H, m), 4.57 (1H, m), 4.77 (1H, m).

(Process 2)

The mixture of the compound (2) (41.5 g, 0.112 mol), potassium acetate (12.1 g, 0.123 mol), and dimethylsulfoxide (125 ml) was heated in an oil bath at 160° C. for 17 h under nitrogen atmosphere. After cooling the reaction mixture, thereto was added water and the mixture was extracted with ether. The ether layer was washed with water, dried over magnesium sulfate, and evaporated. The residue was distilled under reduced pressure to give the colorless oil (3) (29.14 g, 87.2%) showing the boiling point of 153–155° C.

$^1$H-NMR (CDCl$_3$); 1.22 (3H, t, J=6.9 Hz), 1.23 (3H, t, J=6.9 Hz), 1.54–1.96 (12H, m), 2.79 (1H, m), 3.40–3.86 (8H, m), 4.67 (1H, t, J=3.5 Hz), 4.68 (1H, dd, J=7.5, 4.5 Hz).

(Process 3)

To Grignard reagent which was prepared from magnesium (1.12 g, 0.0459 mol), ether (30 ml), 1,2-dibromoethane (0.15 ml, 0.00186 mol), and benzyl bromide (5.24 ml, 0.044 mol) was added a solution of the compound (3) (11.0 g, 0.0367 mol) in ether (33 ml), and the solution was stirred at room temperature for 14 h, then refluxed in an oil bath at 60° C. for 5 h. To the reaction mixture were added in an ice bath aqueous ammonium chloride (3.93 g, 0.0734 mol) solution (40 ml) and 2N sulfuric acid 38 ml, and the resulting mixture was stirred for 30 min. To the reaction mixture was added sodium bicarbonate, the mixture was neutralized and extracted with ether. The ether layer was dried over magnesium sulfate and evaporated to obtain the light brown crude product (4) (15.2 g). The crude product was used in process 4.

(Process 4)

To a suspension of the compound (4) (16.2 g) obtained by the above-mentioned method and N-aminophthalimide (5.95 g, 0.0367 mol) in 95% ethanol (100 ml) was added 1N hydrochloric acid (18.4 ml, 0.0184 mol) and the mixture was refluxed in an oil bath for 30 min. After evaporation of ethanol under reduced pressure, to the residue was added water and the mixture was extracted with chloroform. The organic layer was washed with water, dried over anhydrous magnesium sulfate, subjected to silica gel column chromatography. The fraction eluted with a mixed solvent of 5% acetonitrile-chloroform gave 10.7 g of the crude product. Recrystallization from acetone-isopropyl ether yielded the light yellow crystal (5) (7.20 g, 54.6%) showing the melting point of 127–129° C.

Elemental Analysis; $C_{22}H_{20}N_2O_3$.

Calcd.: C; 73.31, H; 5.52, N; 7.89.

Found: C; 73.31, H; 6.59, N; 7.77.

$^1$H-NMR (CDCl$_3$); 1.85 (2H, m), 2.58 (2H, t, J=7.2 Hz), 3.68 (2H, t, J=6.2 Hz), 3.68 (2H, s), 6.22 (1H, d, J=3.0 Hz), 6.61 (1H, d, J=3.0 Hz), 6.95–7.04 (7H, m), (Process 5)

The mixture of the compound (5) (1.80 g, 5 mmol), hydrazine hydrate (626 mg, 12.6 mmol), and 99.5% ethanol 18 ml was refluxed in an oil bath for 45 min. After evaporation of ethanol under reduced pressure, the residue was treated with toluene to remove the crystal. The toluene layer was washed with water, dried over magnesium sulfate and subjected with alumina column chromatography. The fractions eluted with a mixed solvent of 20% ethyl acetate-toluene were collected to give the colorless oil (6) (1.20 g, 100%).

$^1$H-NMR (CDCl$_3$); 1.80 (2H, m), 2.50 (2H, t, J=7.4 Hz), 3.65 (2H, t, J=6.2 Hz), 4.01 (2H, s), 5.93 (1H, d, J=3.0 Hz), 6.66 (1H, J=3.0 Hz), 7.07–7.28 (5H, m).

(Process 6)

A mixture of the compound (6) (1.20 g, 5 mmol), methyl acetoacetate (681 mg, 6 mmol), p-toluenesulfonic acid monohydrate (48 mg, 0.25 mmol), and chloroform (40 ml) was refluxed in an oil bath for 16 h. The produced water was dehydrated with a Dean-Stark packed with molecular sieves 4A. After cooling the reaction mixture, it was subjected to a silica gel column chromatography. The fractions eluted with 20% acetonitrile-chloroform were collected to give the crude crystal 1.497 g. Recrystallization of the crude crystal from acetone-isopropyl ether obtained the crystal (7) (1.21 g, 81.6%) showing the melting point of 148–149° C.

$^1$H-NMR (CDCl$_3$); 1.68 (2H, m), 2.28 (3H, s), 2.60 (2H, t, J=7.2 Hz), 3.41 (2H, q, J=5.2 Hz), 4.25 (2H, s), 4.42 (1H, t, J=5.2 Hz), 5.84 (1H, s), 6.39 (1H, s), 7.12–7.21 (5H, m), 11.00 (1H, s).

(Process 7)

A mixture of the compound (7) (1.08 g, 3.63 mmol), methyl bromoacetate (0.45 ml, 4.72 mmol), potassium carbonate (652 mg, 4.72 mmol) and dimethylformamide (10 ml) was stirred at room temperature for 1 h 45 min. To the reaction mixture was added water and the resulting mixture was extracted with toluene. The organic layer was washed with water, dried over magnesium sulfate, and subjected to silica gel column chromatography eluted with toluene. The elution 1.18 g was recrystallized from acetone-isopropyl ether to give the compound (8) (1.07 g, 80.1%) as the white crystal showing the melting point of 102–103° C.

Elemental Analysis; C$_{21}$H$_{24}$N$_2$O$_4$;
Calcd.: C; 68.48, H; 6.51, N; 7.58.
Found: C; 68.46, H; 6.57, N; 7.60.

$^1$H-NMR (CDCl$_3$); 1.85 (2H, m), 2.40 (3H, s), 2.72 (2H, t, J=7.2 Hz), 3.61 (2H, t, J=6.2 Hz), 3.84 (3H, s), 4.38 (2H, s), 4.77 (2H, s), 6.63 (1H, a), 6.53 (1H, br.s), 7.12–7.22 (5H, m).

(Process 8)

A mixture of the compound (8) (942 mg, 2.56 mmol), triphenylphosphine (805 mg, 3.07 mmol), carbon tetrachloride (5 ml) and dichloromethane (5 ml) was stirred at room temperature for 4.5 h. The reaction mixture was subjected to silica gel column chromatography and the fractions eluted with chloroform were collected to give the oily compound (9) (808 mg, 81.6%).

$^1$H-NMR (CDCl$_3$); 2.02 (2H, m), 2.39 (3H, s), 2, 78 (2H, t, J=7.4 Hz), 3.49 (2H, t, J=6.6 Hz), 3.83 (3H, s), 4.37 (2H, s), 4.77 (2H, s), 5.62 (1H, s), 6.51 (1H, s), 7.12–7.23 (5H, m).

(Process 9)

To a solution of oxalyl chloride (0.91 ml, 10.5 mmol) in dichloromethane (10 ml) cooled in ice-methanol bath (−14° C.) was added a solution of the compound (9) (808 mg, 2.09 mmol) and N,N-diisopropylethylamine (0.44 ml, 2.51 mmol) in dichloromethane (5 ml), and the solution was stirred at the same temperature for 15 min. After the reaction mixture was poured into a solvent mixed with conc. aqueous ammonia (3 ml) and chloroform (20 ml), the insoluble substances were filtrated and the mixture was extracted with chloroform. The organic layer was washed with water, dried over magnesium sulfate, and subjected to silica gel column chromatography. The fractions eluted with 50% acetonitrile-chloroform were recrystallized from acetone-ethyl acetate to obtain the compound (10) (854 mg, 82.9%) as the light yellow crystal showing the melting point of 194–196° C.

Elemental Analysis: C$_{23}$H$_{24}$ClN$_3$O$_5$.
Calcd.: C; 60.27, H; 5.21, N; 9.21, Cl; 7.89.
Found:C; 60.33, H; 5.28, N; 9.18, Cl; 7.74.

$^1$H-NMR (CDCl$_3$); 2.01 (2H, m), 2.46 (3H, s), 2.96 (2H, t, J=7.7 Hz), 3.54 (2H, t, J=6.4 Hz), 3.82 (3H, s), 4.38 (2H, s), 4.75 (2H, s), 5.52 (1H, br.s), 5.97 (1H, s), 6.63 (1H, br.s), 7.24 (5H, m).

(Process 10)

A mixture of the compound (10) (750 mg, 1.64 mmol), triphenylphosphine (516 mg, 1.97 mmol), potassium iodide (327 mg, 1.97 mmol) and acetonitrile (30 ml) was refluxed for 70 h in an oil bath. Acetonitrile was evaporated, the residue was treated with chloroform, the insoluble substances were filtrated and the filtrate was subjected to silica gel column chromatography. The fractions eluted with 10% acetonitrile-chloroform were collected to the compound (11) (1.32 g, 99.2%) as the light yellow powder.

$^1$H-NMR (CDCl$_3$); 1.82 (2H, m), 2.46 (3H, s), 3.14 (2H, t, J=6.4 Hz), 3.31 (2H, m), 3.82 (3H, s), 4.40 (2H, s), 4.84 (2H, s), 5.78 (1H, br.s), 6.02 (1H, s), 6.86 (1H, br.s), 7.04–7.78 (20H, m).

(Process 11)

The mixture of the compound (11) (1.32 g, 1.63 mmol), DBU(0.61 ml, 4.08 mmol), and dichloromethane (15 ml) was refluxed for 6 h in an oil bath. After to the reaction mixture was added water and the mixture was acidified with 2N hydrochloric acid, the resulting mixture was extracted with chloroform. The organic layer was washed with water, dried over magnesium sulfate, and subjected to a silica gel column chromatography. The fractions eluted with 40% acetonitrile-chloroform was collected and recrystallized from acetone-isopropyl ether to give the compound (12) (375 mg, 56.9%) as light yellow crystal showing the melting point 181–183° C.

Elemental Analysis: C$_{23}$H$_{23}$N$_3$O$_4$.
Calcd.:C; 68.27, H; 5.64, N; 10.41.
Found: C; 68.13, H; 5.72, N; 10.37.

$^1$H-NMR (d$_6$-DMSO); 2.33 (2H, m), 2.38 (3H, s), 2.63 (2H, t, J=7.2 Hz), 3.81 (3H, s), 4.21 (2H, s), 4.74 (2H, s), 5.62 (1H, s), 5.63 (2H, br), 6.42 (1H, t, J=5.1 Hz), 7.14–7.25 (5H, m).

(Process 12)

To a solution of the compound (12) (37 mg, 0.091 mmol) in methanol (3 ml) was added 1N aqueous sodium hydroxide solution (0.18 ml, 0.18 mmol) and the reaction mixture was stirred at room temperature for 45 min. To the mixture was added 1N hydrochloric acid (0.23 ml, 0.23 mmol) and the resulting mixture was evaporated under reduced pressure. The precipitated crystal was filtrate and the crystal was recrystallized from tetrahydrofuran-ethyl acetate to give the compound (I-1) (34 mg, 94.4%) as light yellow crystal showing the melting point 256–258° C. (decomp.p.).

Elemental Analysis: C$_{22}$H$_{21}$N$_3$O$_4$.
Calcd.: C; 67.33, H; 5.46, N; 10.69.
Found: C; 67.50, H; 5.41, N; 10.74.

$^1$H-NMR (d$_6$-DMSO); 2.25 (2H, m), 2.32 (3H, s), 2.58 (2H, t, J=7.6 Hz), 4.26 (2H, s), 4.75 (2H, s), 6.01 (1H, s), 6.08 (1H, t, J=4.8 Hz), 6.91 (1H, br.s), 7.14–7.29 (5H, m), 7.32 (1H, br.s).

The compound (I-2) to (I-10) were synthesized by the same reaction described in Example 1. The physical data are shown in Table 1 and Table 2.

TABLE 1

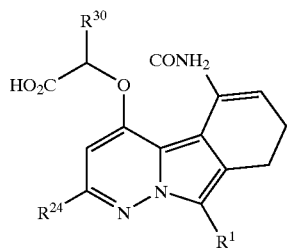

| Example No. | Compound No. | $R^1$ | $R^{30}$ | $R^{24}$ | m.p. (° C.) | $^1$H-NMR (CDCl$_3$) |
|---|---|---|---|---|---|---|
| 2 | I-2 | Bn | Me | Me | 247–248 (d) | 1.60(3H, d, J=7.0Hz), 2.27(2H, m), 2.31(3H, s), 2.59(2H, m), 4.25 (2H, s), 4.98(1H, q, J=7.0Hz), 5.87(1H, s), 6.18(1H, t, J=4.6Hz), 7.06(1H, br.s), 7.22(5H, m), 7.52 (1H, br.s), 12.96(1H, br) |
| 3 | I-3 | 4-Me-Bn | H | Me | 273–275 (d) | 2.22(3H, s), 2.24(2H, m), 2.32(3H, s), 2.57(2H, t, J=7.3Hz), 4.20 (2H, s), 4.75(2H, s), 6.00(1H, s), 6.08(1H, t, J=4.8Hz), 6.93(1H, br.s), 7.04(2H, d, J=8.1Hz), 7.09 (2H, d, J=8.1Hz), 7.33(1H, br.s) |
| 4 | I-4 | 4-Me-Bn | Me | Me | 254–255 (d) | 1.60(3H, d, J=6.9Hz), 2.27(2H, m), 2.22(3H, s), 2.30(3H, s), 2.59 (2H, m), 4.20(2H, s), 4.98(1H, q, J=6.9Hz), 5.86(1H, s), 6.18(1H, t, J=4.8Hz), 7.04(2H, d, J=8.4Hz), 7.07(2H, d, J=8.4Hz), 7.53(1H, br.s) |
| 5 | I-5 | 4-Cl-Bn | H | Me | 279–281 (d) | 2.26(2H, m), 2.31(3H, s), 2.59(2H, t, 7.2Hz), 4.25(2H, s), 4.75(2H, s), 6.02(1H, s), 6.09(1H, t, J=4.7Hz), 6.94(1H, br.s), 7.22(2H, d, J=8.7Hz), 7.30(2H, d, 8.7Hz), 7.34(1H, br.s), 13.11(1H, br.s) |

TABLE 2

| Example No. | Compound No. | $R^1$ | $R^{30}$ | $R^{24}$ | m.p. (° C.) | $^1$H-NMR (CDCl$_3$) |
|---|---|---|---|---|---|---|
| 6 | I-6 | 4-Cl-Bn | Me | Me | 258–260 (d) | 1.60(3H, d, J = 6.9 Hz), 2.26 (2H, m), 2.30(3H, s), 2.61(2H, m), 4.25 (2H, s), 4.99(1H, q, J = 6.9 Hz), 5.88(1H, s), 6.19(1H, t, J = 4.8 Hz), 7.08(1H, br.s), 7.22(2H, d, J = 8.4 Hz), 7.30(2H, d, J = 8.4 Hz), 7.54 (1H, br.s), 12.98(1H, br.s) |
| 7 | I-7 | 3-MeO-Bn | H | Me | 255–257 (d) | 2.25(2H, m), 2.33(3H, s), 2.58(2H, t, J = 7.5 Hz), 3.69(3H, s), 4.22 (2H, s), 4.75(2H, s), 6.02 (1H, s), 6.08(1H, t, J = 4.8 Hz), 6.71–6.83 (3H, m), 6.93(1H, br.s), 7.15 (1H, t, J = 8.0 Hz), 7.33 (1H, br.s), 13.10(1H, br.s) |
| 8 | I-8 | 8-MeO-Bn | Me | Me | 229–231 | 1.60(3H, d, J = 6.9 Hz), 2.28(2H, m), 2.32(3H, s), 2.61(2H, m), 3.69 (3H, s), 4.23 (2H, s), 4.99 (1H, q, J = 6.9 Hz), 5.88 (1H, s), 6.18(1H, t, J = 4.8 Hz), 6.72–6.83(3H, m), 7.08(1H, br.s), 7.15 (1H, t, J = 7.8 Hz), 7.54 (1H, br.s), 12.98(1H, br.s) |
| 9 | I-9 | Bn | H | Ph | 270–272 | 2.30(2H, m), 2.69(2H, m), 4.36(2H, s), 4.92 (2H, s), 6.14(1H, t, J = 5.1 Hz), 6.63(1H, s), 6.93(1H, br.s), 7.13–7.35 (6H, m), 7.46–7.54(3H, m), 7.98–8.02(2H, m) |
| 10 | I-10 | 3-MeO-Bn | H | Ph | 261–263 | 2.30(2H, m), 2.70(2H, t, J = 7.5 Hz), 3.67(3H, s), 4.33(2H, s), 4.94(2H, s), 6.14(1H, t, J = 4.8 Hz), 6.65(1H, s), 6.71–6.94(5H, m), 7.14–7.19 (1H, m), 7.36(1H, br.s), 7.47–7.54(3H, m), 8.02–8.05(2H, m) |

Example 11
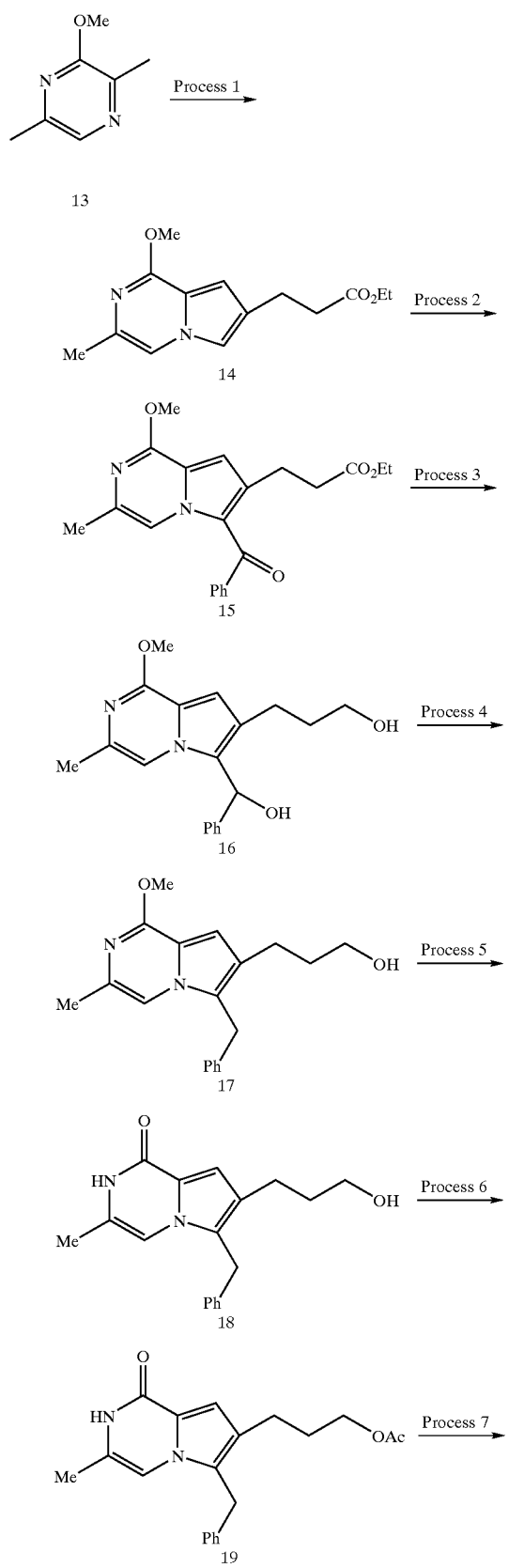
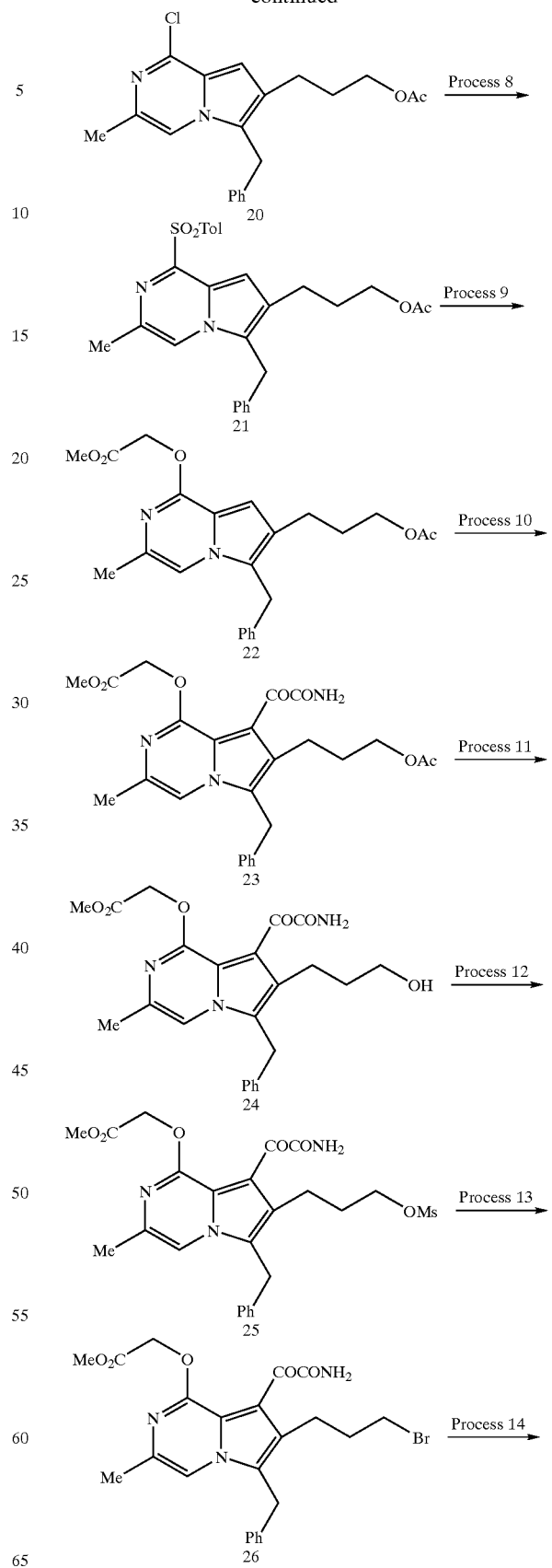

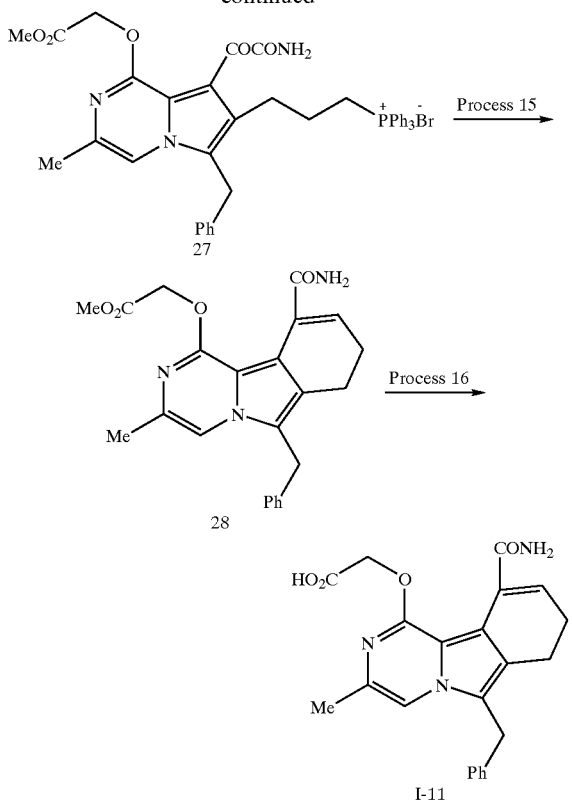

(Process 1)

The mixture of 3-methoxy-2,5-dimethylpyrazine (13) (13.71 g, 99.2 mmol) and ethyl 5-bromo-4-oxopentanate (24.34 g, 109.1 mmol) was stirred at 60° C. for 16 h. To a solution of the reaction mixture in acetonitrile (143 ml) was added DBU (23 ml, 153.8 mmol) and the mixture was refluxed for 2 h. The reaction mixture was concentrated and poured into water and the mixture was extracted with ethyl acetate. The organic layer was washed with brine, dried over magnesium sulfate and evaporated. The residue was purified with silica gel column chromatography (hexane:ethyl acetate=9:1) to give the product (14) (10.57 g, 40.6%) as light yellow oil.

$^1$H-NMR (CDCl$_3$); 1.24 (3H, t, J=7.2 Hz), 2.26 (3H, s), 2.63 (2H, t, J=7.5 Hz), 2.97 (2H, t, J=7.5 Hz), 4.03 (3H, s), 4.13 (2H, q, J=7.2 Hz), 6.53 (1H, s), 7.07 (1H, m), 7.22 (1H, s).

(Process 2)

To a suspension of aluminum chloride (11.24 g, 84.3 mmol) in chlorobenzene (27 ml) was added benzoyl chloride (9.78 ml. 84.3 mmol) in an ice bath, and the reaction mixture was stirred in same condition for 10 min. To the reaction mixture was added gradually the compound (14) (7.37 g, 28.1 mmol) and furthermore the reaction mixture was stirred in the same condition for 3 h. The reaction mixture was poured into a solvent mixed with ice, 28% aqueous ammonia and ethyl acetate and then insoluble substances were filtrated. The filtrate was extracted with ethyl acetate, then the organic layer was washed with water and dried over magnesium sulfate. After evaporation of the solvent, the residue was purified with silica gel column chromatography (hexane:ethyl acetate=9:1). The product (15) (3.49 g, 33.9%) was obtained as yellow crystal.

$^1$H-NMR (CDCl$_3$); 1.16 (3H, t, J=7.2 Hz), 2.35 (3H, s), 2.40–2.48 (2H, m), 2.58–2.66 (2H, m), 4.03 (2H, q, J=7.2 Hz), 4.08 (3H, s), 6.61 (1H, s), 7.44–7.60 (3H, m), 7.64–7.70 (2H, m), 8.50 (1H, s).

(Process 3)

To a solution of the compound (15) (5.49 g, 15.0 mmol) in a mixed solvent of diethyl ether (100 ml) and tetrahydrofuran (50 ml) was added gradually lithium aluminum hydride (1 g, 26.4 mmol) at room temperature and the mixture was stirred for 3 h. After the reaction mixture was diluted with tetrahydrofuran (30 ml) and cooled in an ice bath, to the mixture was added water (2.5 ml) gradually, then the mixture was stirred at room temperature for 1 h. The precipitated inorganic substances were filtrated and washed with tetrahydrofuran. After evaporation of the solvent, the residue was dissolved in ethyl acetate and dried over magnesium sulfate. Evaporation of the solvent gave the product (16) (5.0 g, 100%). It is proceeded to the further reaction without purification.

(Process 4)

To a suspension of aluminum chloride (4.0 g, 30 mmol) in tetrahydrofuran (95 ml) was added borane-t-butylamine complex (5.21 g, 60 mmol) in an ice bath, and the mixture was stirred for 10 min. Next, a solution of the compound (16) (5.0 g, 16.0 mmol) in tetrahydrofuran 30 ml was added to it in the same condition and the mixture was stirred at room temperature for 1 h. It war poured into 2N hydrochloric acid and the resulting mixture was extracted with ethyl acetate. The organic layer was washed with brine, dried over magnesium sulfate and evaporated. The residue was purified with silica gel column chromatography (toluene:ethyl acetate=5:1) to yield the product (17) (4.71 g, 100%) as light yellow oil.

$^1$H-NMR (CDCl$_3$); 1.23 (1H, br.s), 1.82–1.94 (2H, m), 2.20 (3H, s), 2.73 (2H, t, J=7.5 Hz), 3.60–3.70 (2H, m), 4.04 (3H, s), 4.20 (2H, s), 6.65 (1H, s), 6.96–7.03 (3H, m), 7.15–7.29 (3H, m).

(Process 5)

The mixture of the compound (17) (4.71 g, 15.0 mmol) and conc. hydrochloric acid (88 ml) was refluxed for 70 min. The reaction mixture was diluted with water and extracted with a mixed solvent of chloroform-methanol (9:1). The organic layer was washed with brine, dried over magnesium sulfate and evaporated. The residue was washed with ethyl acetate-diethyl ether to give the product (18) (3.60 g, 81%) as colorless powder.

$^1$H-NMR (d$_6$-DMSO); 1.61–1.72 (2H, m), 1.97 (3H, s), 2.54 (2H, t, J=7.8 Hz), 3.40 (2H, q, J=6.6 Hz), 4.14 (2H, s), 4.42 (1H, t, J=5.1 Hz), 6.72 (1H, s), 6.87 (1H, s), 7.04–7.31 (5H, m), 10.37 (1H, br.s).

(Process 6)

To a solution of the compound (18) (3.53 g, 11.9 mmol) in pyridine (71 ml) was added acetic anhydride (3.37 ml, 35.7 mmol), and the mixture was stirred at room temperature for 6.5 h. After the reaction mixture was diluted with water and to it was added in an ice bath 1N hydrochloric acid to be acid, the resulting mixture was extracted with ethyl acetate. The organic layer was washed with water, brine successively, dried over magnesium sulfate and evaporated. The residue was recrystallized from dichloromethane-diethyl ether to give the product (19) (3.86 g, 95.6%) as colorless crystal.

m.p.: 160–161° C.;

$^1$H-NMR (CDCl$_3$); 1.87–1.92 (2H, m), 2.01 (3H, s), 2.11 (3H, s), 2.65 (2H, t, J=7.5 Hz), 4.06 (2H, t, J=6.3 Hz), 4.13 (3H, s), 6.46 (1H, s), 6.98–7.04 (3H, m), 7.17–7.32 (3H, m), 10.04 (1H, br.s).

(Process 7)

A mixture of the compound (19) (3.94 g, 11.64 mmol) and phosphorus oxychloride (31 ml) was stirred at 80° C. for 45 min. After evaporation of phosphorus oxychloride under reduced pressure, the residue was dissolved in ethyl acetate. The organic layer was washed with saturated sodium hydrogen carbonate aqueous solution and brine, dried over magnesium sulfate, and evaporated. The residue was purified with silica gel column chromatography (toluene:ethyl acetate=7:1) to obtain the product (20) (4.25 g, 100%) as light yellow oil.

$^1$H-NMR (CDCl$_3$); 1.93–2.05 (2H, m), 2.02 (3H, s), 2.29 (3H, s), 2.77 (2H, t, J=7.5 Hz), 4.09 (2H, t, J=6.3 Hz), 4.23 (2H, s), 6.80 (1H, s), 6.95–7.01 (2H, m), 7.18–7.32 (4H, m).

(Process 8)

To a solution of the compound (20) (4.25 g, 11.64 mmol) in ethanol (62 ml) was added sodium p-toluenesulfinate (4.15 g, 23.3 mmol), and the mixture was refluxed for 36 h. To the reaction mixture was poured into water and the resulting mixture was extracted with ethyl acetate. The organic layer was washed with brine, dried over magnesium sulfate, and evaporated. The residue was purified with silica gel column chromatography (ethyl acetate) to obtain the product (21) (4.86 g, 87.5%) as light yellow crystal.

m.p.: 141–142° C.;

$^1$H-NMR (CDCl$_3$); 1.97–2.09 (2H, m), 2.04 (3H, s), 2.31 (3H, s), 2.41 (3H, s), 2.82 (2H, t, J=7.5 Hz), 4.10 (2H, t, J=6.3 Hz), 4.24 (2H, s), 6.92–6.98 (2H, m), 7.17–7.35 (6H, m), 7.46 (1H, s), 8.01 (2H, d, J=8.1 Hz).

(Process 9)

To a solution of methyl glycolate (3.85 ml, 49.9 mmol) in tetrahydrofuran (120 ml) was added potassium t-butoxide (3.36 g, 29.9 mmol), the mixture was stirred at room temperature for 30 min. Next, it was cooled in an ice bath, the compound (21) (4.75 g, 9.97 mmol) was added to it, and the mixture was stirred for 40 min. The reaction mixture was poured into water and the resulting mixture was extracted with ethyl acetate. The organic layer was washed with brine, dried over magnesium sulfate, and evaporated. The residue was purified with silica gel column chromatography (hexane:ethyl acetate=1:1) to obtain the product (22) (2.71 g, 66.2%) as light yellow oil.

$^1$H-NMR (CDCl$_3$); 1.90–2.02 (2H, m), 2.01 (3H, s), 2.14 (3H, s), 2.72 (2H, t, J=7.5 Hz), 3.77 (3H, s), 4.07 (2H, t, J=6.6 Hz), 4.18 (2H, s), 5.01 (2H, s), 6.74 (1H, s), 6.96–7.03 (3H, m), 7.16–7.30 (3H, m).

(Process 10)

To a solution of the compound (22) (2.60 g, 6.34 mmol) in dichloromethane (78 ml) were added N-methyl morpholine (1.39 ml, 12.6 mmol) and oxalyl chloride (1.1 ml, 12.6 mmol) in an ice bath and the mixture was stirred at room temperature for 2.5 h. Next, the reaction mixture was poured into 28% aqueous ammonia (78 ml), the resulting mixture was stirred for 10 min and extracted with dichloromethane. The organic layer was washed with brine, dried over magnesium sulfate, and evaporated. The residue was purified with a silica gel column chromatography (ethyl acetate) to give the product (23) (2.42 g, 79.3%) as light yellow crystal.

m.p.: 157–158° C.;

$^1$H-NMR (CDCl$_3$); 1.86–1.97 (2H, m), 2.02 (3H, s), 2.18 (3H, s), 2.84–2.92 (2H, m), 3.76 (3H, s), 4.07 (2H, t, J=6.3 Hz), 4.21 (2H, s), 4.97 (2H, s), 5.66 (1H, br.s), 6.64 (1H, br.s), 7.02–7.08 (3H, m), 7.19–7.33 (3H, m).

(Process 11)

To a solution of the compound (23) (2.66 g, 5.63 mmol) in methanol (67 ml) and tetrahydrofuran (13 ml) was added 5N-hydrochloric acid (27.5 ml), and the mixture was stirred at room temperature for 7 h. The reaction mixture was diluted with water and extracted with ethyl acetate. The organic layer was washed with brine, dried over magnesium sulfate, and evaporated. The residue was purified with silica gel column chromatography (ethyl acetate:methanol=19:1) to give the product (24) (2.0 g, 82.3%) as yellow powder.

$^1$H-NMR (CDCl$_3$); 1.75–1.86 (2H, m), 2.18 (3H, s), 2.93 (2H, t, J=7.2 Hz), 3.57 (2H, t, J=5.7 Hz), 3.76 (3H, s), 4.23 (2H, s), 4.98 (2H, s), 5.75 (1H, br.s), 6.67 (1H, br.s), 6.99–7.09 (3H, m), 7.19–7.32 (3H, m).

(Process 12)

To a solution of the compound (24) (1.88 g, 4.29 mmol) in dichloromethane (54 ml) were added triethylamine (0.90 ml, 6.43 mmol), methanesulfonyl chloride (0.50 ml, 6.43 mmol) in an ice bath, and the mixture was stirred for 30 min. The reaction mixture was poured into ice-water and then the resulting mixture was acidified with 1N hydrochloric acid and extracted with dichloromethane. The organic layer was washed with brine, dried over magnesium sulfate, evaporated and the product (25) (2.09 g, 94%) was obtained as yellow powder. It was subjected to the next reaction without any purification.

(Process 13)

To a solution of the compound (25) (2.09 g, 4.03 mmol) in dimethylformamide (38 ml) was added lithium bromide (1.4 g, 16.1 mmol), the mixture was stirred at 50° C. for 2 h 45 min. The reaction mixture was poured into water and the resulting mixture was extracted with ethyl acetate. The organic layer was washed with brine, dried over magnesium sulfate, and evaporated. The residue was purified with silica gel column chromatography (toluene:ethyl acetate=1:1) to give the product (26) (1.62 g, 75.8%).

m.p.: 157–158° C.;

$^1$H-NMR (CDCl$_3$); 2.08–2.19 (2H, m), 2.18 (3H, s), 2.97 (2H, t, J=7.5 Hz), 3.43 (2H, t, J=6.6 Hz), 3.76 (3H, s), 4.26 (2H, s), 4.97 (2H, s), 6.64 (1H, br.s), 6.62 (1H, br.s), 7.03–7.11 (3H, m), 7.20–7.33 (3H, m).

(Process 14)

To a suspension of the compound (26) (1.96 g, 3.90 mmol) in acetonitrile (37 ml) was added triphenylphosphine (1.55 g, 5.91 mmol), and the mixture was refluxed for 18 h. After evaporation of acetonitrile, the residue was washed with ethyl acetate-ether to give the compound (27) (2.71 g, 90.9%) as yellow powder. It was subjected to the next reaction without any purification.

(Process 15)

To a solution of the compound (27) (2.71 g, 3.54 mmol) in acetonitrile (70 ml) was added DBU (1.32 ml, 8.83 mmol), and the mixture was stirred at room temperature for 3 h 40 min. The reaction mixture was poured into 1N hydrochloric acid and the resulting mixture was extracted with ethyl acetate. The organic layer was washed with brine, dried over magnesium sulfate, and evaporated. The residue was purified with silica gel column chromatography (ethyl acetate:methanol=19:1) to give the product (28) (696 mg, 48.4%) as colorless crystal.

m.p.: 178–180° C.;

$^1$H-NMR (CDCl$_3$); 2.13 (3H, d, J=0.9 Hz), 2.32–2.42 (2H, m), 2.68 (2H, t, J=7.5 Hz), 3.75 (3H, s), 4.16 (2H, s), 4.97 (2H, s), 5.40–5.95 (2H, br), 6.55 (1H, t, J=4.8 Hz), 6.99 (1H, d, J=0.9 Hz), 7.05–7.10 (2H, m), 7.18–7.32 (3H, m).

(Process 16)

To a solution of the compound (28) (395 mg, 0.974 mmol) in tetrahydrofuran (15 ml) was added 1N sodium hydroxide aqueous solution (3.88 ml), and the mixture was stirred at room temperature for 35 min. To the reaction mixture was added 1N hydrochloric acid 4 ml and the resulting mixture was extracted with a mixed solvent of chloroform and methanol (9:1). The organic layer was washed with brine, dried over magnesium sulfate, and evaporated. The residue was recrystallized from dichloromethane-methanol-ether to give the product (I-11) (331 mg, 86.8%) as colorless crystal.
m.p.: 204–206° C.;
$^1$H-NMR (d$_6$-DMSO); 2.11 (1H, s), 2.23–2.34 (2H, m), 2.64 (2H, t, J=7.5 Hz), 4.24 (2H, s), 4.76 (2H, s), 6.19 (1H, t, J=4.8 Hz), 7.01 (1H, br.s), 7.13–7.22 (3H, m), 7.24–7.32 (2H, m), 7.41 (1H, br.s), 7.51 (1H, s), 12.72 (1H, br).

The compounds (I-12) to (I-14) were synthesized by the same reaction described in Example 11. The physical data are shown in Table 3.

Tris-HCl (3.94 g/L)
pH 7.5 (adjusted with NaOH)
Enzyme Buffer—
 0.05 M-AcONa
 0.2 M-NaCl
 pH 4.5 (adjusted with acetic acid)
DTNB—
 198 mg of 5,5'-dithiobis-2-benzoic acid (manufactured by Wako Pure Chemicals) is dissolved in 100 ml of H$_2$O
 pH 7.5 (adjusted with NaOH)

TABLE 3

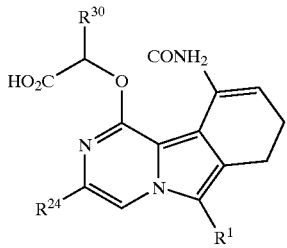

| Example No. | Compound No. | R$^1$ | R$^{30}$ | R$^{24}$ | m.p. (° C.) | $^1$H-NMR (d6-DMSO) |
|---|---|---|---|---|---|---|
| 12 | I-12 | Bn | H | H | 199–202 (d) | 2.25–2.35(2H, m), 2.67(2H, t, J=7.5Hz), 4.27(2H, s), 4.75(2H, s), 6.22(1H, t, J=4.8Hz), 6.94(1H, d, J=4.8Hz),6.99(1H, br.s), 7.14–7.32(5H, m), 7.41(1H, br.s), 7.63 (1H, d, J=4.8Hz), 12.73(1H, br). |
| 13 | I-13 | Bn | Me | Me | 183–185 (d) | 1.54(3H, d, J=7.2Hz), 2.09(3H, d, J=0.6Hz), 2.14–2.40(2H, m), 2.50–2.76(2H, m), 4.23(2H, s), 5.98(1H, q, J=7.2Hz), 6.25(1H, t, J=5.1Hz), 7.07(1H, br.s), 7.12–7.32(5H, m), 7.48(1H, d, J=0.6Hz), 7.53(1H, br.s), 12.47(1H, br). |
| 14 | I-14 | CH$_{2C}$-Hex | Me | Me | 184–185 (d) | 0.90–1.24(5H, m), 1.44–1.72(6H, m), 1.53(3H, d, J=6.9Hz), 2.15 (3H, d, J=0.6Hz), 2.13–2.38(2H, m), 2.40–2.70(2H, m), 2.69(2H, d, J=7.2Hz), 5.21(1H, q, J=6.9Hz), 6.22(1H, t, J=4.8Hz), 7.07(1H, br.s), 7.54(1H, br.s), 7.54(1H, s), 12.47(1H, br). |

Test Example: Inhibition Test of Human Secretory Phospholipase A$_2$

Analytical Experiment

In order to identify and evaluate an inhibitor of recombinant human secretory phospholipase A$_2$, the following chromogenic assay is utilized. The assay herein has been applied for high volume screening wherein 96 well microtiterplate is used. A general explanation for such assay is described in "Analysis of Human Synovial Fluid Phospholipase A$_2$ on Short Chain Phosphatidylcholine-Mixed Micelles: Development of a Spectrophotometric Assay Suitable for a Micortiterplate Reader" (Analytical Biochemistry, 204, pp 190–197, 1992 by Laure. J. Reynolds. Lori L. Hughes and Edward A. Dennis: the disclosure of which is incorporated herein for reference.
Reagents:
 Reaction Buffer—
  CaCl$_2$.6H$_2$O (2.19 g/L)
  KCl (7.455 g/L)
  Bovine Serum Albumin (fatty acid free) (1 g/L) (Sigma A-7030)

Substrate Solution—
 100 mg of racemic 1,2-bis(heptanoylthio)-1,2-dideoxy-sn-glycero-3-phosphorylcholine is dissolved in 1 ml of chloroform.
Triton-X 100—
 624.9 mg of Triton-X 100 is dissolved in 100 ml of the reaction buffer.
Enzyme Solution—
 Type I enzyme: sPLA$_2$ solution (330 ng/μl) (described in A. Kanda et. al., Biochimica et Biophysica Acta. 1171 (1992) 1–10) is dissolved in the assay (enzyme solution 27 μl is diluted with 1973 μl of the reaction buffer).
 Type II enzyme: 1 mg of sPLA$_2$ is dissolved in 1 ml of an enzyme buffer. Thereafter, the solution is maintained at 4° C. In the assay, 5 >l of the solution is diluted with 1995 μl of the reaction buffer to be used.
 Type V and Type X enzymes: cDNA sequences encoding human type V and Type X sPLA$_2$ (Chen et., al., J. Biol. Chem., 1994. 269, 2365–2368 and Cupillard et., al., J.

Biol. Chem., 1997, 272, 15745–15762) were inserted into downstream of promoter of pSVL SV40 Late Promoter Expression Vector (Amersham Pharmacia Biotech K. K.), mammalian cell expression vector, forwardly. The recombinant expression vectors were transfected into CHO host cells by LipofectAMINE regent (Gibco BRL.) according to the attached manual and the cells expressed each of human type V and type X sPLA2 stably. After each expressing cells were cultured in σ-MEM medium including 10% fetal serum albumin for 3 days, the cells supernatant were collected and measured enzymatic activity.

Enzyme Reaction: for 1 Plate of Microtiterplate
1) 0.106 ml of the substrate solution is put in a centrifugal tube, and nitrogen gas is jetted to remove the solvent. 0.54 ml of Triton-X 100 is added thereto, the mixture is stirred, thereafter it is sonified in a bath type sonification to dissolve. To the resulting product are added 17.8 ml of the reaction buffer and 0.46 ml of DTNB, and 0.18 ml each of the admixture is poured to wells of the 96 well microtiterplate.
2) 10 μl of a test compound (or solvent blank) are added in accordance with alignment of plates which has been previously set.
3) Incubation is effected at 40° C. for 15 minutes.
4) 90 ng/well in case of human type I enzyme, 50 ng/well in case of human type II enzyme, 40 μl/well in case of human type V enzyme, 15 μl/well in case of human type X enzyme were reacted.
5) Changes in absorbancy for 30 minutes for humane type I, type II, and type X enzyme and for 45 min for human type V enzyme, are measured by a plate reader, and inhibition activity was calculated (OD: 405 nm).
6) $IC_{50}$ was determined by plotting log concentration with respect to inhibition values within 10% to 90% inhibiting range.

The result is shown in Table 4.

TABLE 4

| Compound No. | Type I $IC_{50}$ (μM) | Type II $IC_{50}$ (μM) | Type V $IC_{50}$ (μM) | Type X $IC_{50}$ (μM) |
| --- | --- | --- | --- | --- |
| I-1 | 0.170 | 0.007 | 0.002 | 0.004 |
| I-2 | 0.079 | 0.015 | 0.003 | 0.004 |
| I-3 | 0.460 | 0.011 | 0.002 | 0.010 |
| I-4 | 0.139 | 0.021 | 0.002 | 0.007 |
| I-5 | 0.147 | 0.008 | 0.001 | 0.006 |
| I-6 | 0.086 | 0.017 | 0.001 | 0.005 |
| I-7 | 0.215 | 0.010 | 0.002 | 0.016 |
| I-8 | 0.076 | 0.023 | 0.002 | 0.012 |
| I-9 | 0.051 | 0.008 | 0.0002 | 0.001 |
| I-10 | 0.049 | 0.006 | 0.0002 | 0.002 |
| I-11 | 0.234 | 0.009 | 0.001 | 0.006 |
| I-12 | 0.086 | 0.008 | 0.002 | 0.004 |
| I-13 | 0.093 | 0.019 | 0.004 | 0.007 |
| I-14 | 0.057 | 0.014 | 0.001 | 0.001 |

Formulation Example

It is to be noted that the following Formulation Examples 1 to 9 are mere illustration, but not intended to limit the scope of the invention. The term "active ingredient" means the compounds represented by the formula (I), the prodrugs thereof, their pharmaceutical acceptable salts, or their solvates.

Formulation Example 1

Hard gelatin capsules are prepared using of the following ingredients:

| | Dose (mg/capsule) |
| --- | --- |
| Active ingredient | 250 |
| Starch, dried | 200 |
| Magnesium stearate | 10 |
| Total | 460 mg |

Formulation Example 2

A tablet is prepared using of the following ingredients:

| | Dose (mg/tablet) |
| --- | --- |
| Active ingredient | 250 |
| Cellulose, microcrystals | 400 |
| Silicon dioxide, fumed | 10 |
| Stearic acid | 5 |
| Total | 665 mg |

The components are blended and compressed to form tablets each weighing 665 mg.

Formulation Example 3

An aerosol solution is prepared containing the following components:

| | Weight |
| --- | --- |
| Active ingredient | 0.25 |
| Ethanol | 25.75 |
| Propellant 22 (chlorodifluoromethane) | 74.00 |
| Total | 100.00 |

The active compound is mixed with ethanol and the admixture added to a portion of the propellant 22, cooled to −20° C. and transferred to filling device. The required amount is then fed to stainless steel container and diluted with the reminder of the propellant. The valve units are then fitted to the container.

Formulation Example 4

Tablets, each containing 60 mg of active ingredient, are made as follows.

| | |
| --- | --- |
| Active ingredient | 60 mg |
| Starch | 45 mg |
| Microcrystals cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve, and the mixed thoroughly.

The aqueous solution containing polyvinylpyrrolidone is mixed with the resultant powder, and the admixture then is passed through a No. 14 mesh U.S. sieve. The granules so produced are dried at 50° C. and passed through a No. 18 mesh U.S. sieve. The sodium carboxymethyl starch, magnesium stearate, and talc, previously passed through No. 60 mesh U.S. sieve, are then added to the granules which, after mixing, are compressed on a tablet machine to yield tablets each weighing 150 mg.

Formulation Example 5

Capsules, each containing 80 mg of active ingredient, are made as follows:

| Active ingredient | 80 mg |
|---|---|
| Starch | 59 mg |
| Microcrystals cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation Example 6

Suppository, each containing 225 mg of active ingredient, are made as follows:

| Active ingredient | 225 mg |
|---|---|
| Saturated fatty acid glycerides | 2000 mg |
| Total | 2225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation Example 7

Suspensions, each containing 50 mg of active ingredient per 5 ml dose, are made as follows:

| Active ingredient | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 U.S. sieve, and mixed with the sodium carboxymethyl cellulose and syrup to form a smooth paste. The benzoic acid solution, flavor and color are diluted with a portion of the water and added, with stirring. Sufficient water is then added to produce the required volume.

Formulation Example 8

An intravenous formulation may be prepared as follows:

| Active ingredient | 100 mg |
|---|---|
| Isotonic saline | 1000 ml |

The solution of the above ingredients generally is administered intravenously to a subject at a rate of 1 ml per minute.

Formulation Example 9

Composition of lyophilized preparations (in 1 vial) is made as follows:

| Active ingredient | 127 mg |
|---|---|
| Trisodium citrate dihydrate | 36 mg |
| Mannitol | 180 mg |

The above materials are dissolved in water for injection such that the concentration of Active ingredient is 10 mg/g. The primary freezing step is done for 3 hours at −40° C., the heat treating step for 10 hours at −10° C., and the re-freezing step for 3 hours at −40° C. Then, the primary drying step is performed for 60 hours at 0° C., 10 Pa and the secondary drying step for 5 hours at 60° C., 4 Pa. Thus the lyophilized preparation is obtained.

Industrial Applicability

The compounds according to the present invention have $sPLa_2$ inhibiting activity to $sPLA_2$-mediated fatty acid (such as arachidonic acid) release, whereby it is effective for treating septic shock and the like.

What is claimed is:
1. A compound represented by the formula (I);

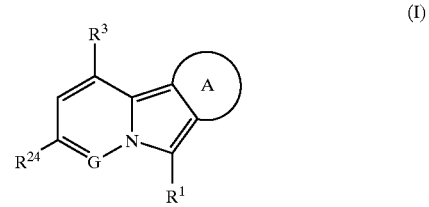

wherein E is N or C—$R^4$;
when E is N, G is C—$R^{25}$, or when E is C—$R^4$, G is N;
$R^1$ is a group selected from (a) C1 to C20 alkyl, C1 to C20 alkenyl, C1 to C20 alkynyl, carbocyclic groups, and heterocyclic groups, and (b) the groups represented by (a) each substituted independently with at least one group selected from non-interfering substituents, or (c) —($L^1$)—$R^5$, wherein $L^1$ is a divalent linking group of 1 to 18 atom(s) selected from hydrogen atom(s), nitrogen atom(s), carbon atom(s), oxygen atom(s), and sulfur atom(s), and $R^5$ is a group selected from the groups (a) and (b);
one of $R^3$ and $R^4$ is —($L^2$)-(acidic group), wherein $L^2$ is an acid linker having an acid linker length of 1 to 5 and the other is a hydrogen atom, and the acidic group is represented by the formula:

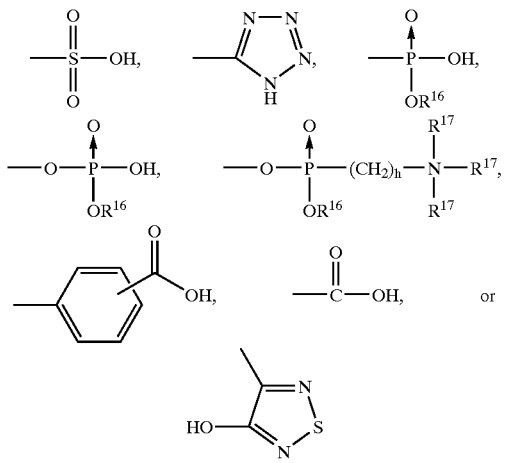

wherein $R^{16}$ is a hydrogen atom, a metal, or C1 to C10 alkyl; each $R^{17}$ is independently a hydrogen atom or C1 to C10 alkyl; h is an Integer from 1 to 8;

wherein A ring is a group represented by the formula:

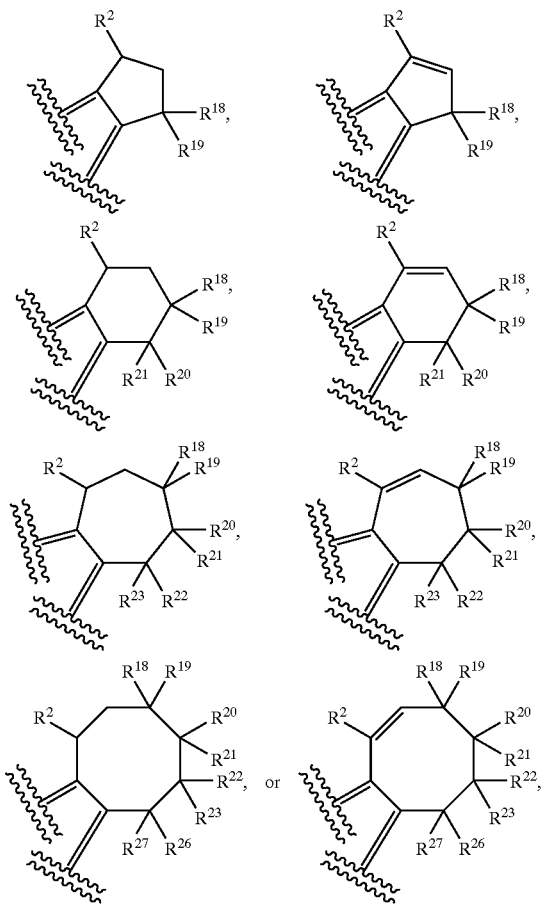

wherein $R^2$ is $CONH_2$, $CONHNH_2$ or $CSNH_2$;
$R^{18}$, $R^{19}$, $R^{20}$, $R^{21}$, $R^{22}$, $R^{23}$, $R^{26}$, and $R^{27}$ are each independently a hydrogen atom, or lower alkyl;
$R^{24}$ and $R^{25}$ are each independently a hydrogen atom, C1 to C6 alkyl, aryl, a halogen or aralkyl;

its $C_1$–$C_8$ alkyl, acyloxyalkyl, and alkyloxycarbonyloxyalkyl ester, its pharmaceutically acceptable salt, or hydrate thereof.

2. A compound represented by the formula (II):

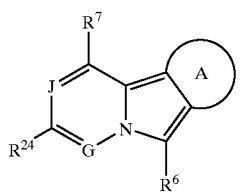

(II)

wherein $R^{24}$ and A ring are as defined in claim 1;
J is N or C—$R^3$; when J is N, G is C—$R^{25}$ (wherein $R^{25}$ is above is a hydrogen atom, C1 to C6 alkyl, aryl, a halogen or aralkyl), or when J is C—$R^8$, G is N;
$R^6$ is —$(CH_2)_m$—$R^9$ wherein m is an integer from 1 to 6, and $R^9$ is (d) a group represented by the formula:

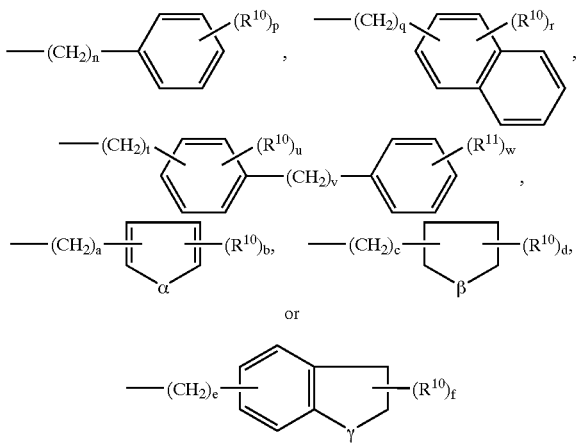

or wherein a, c, e, n, q, t and v are each independently 0, 1, or 2; $R^{10}$ and $R^{11}$ each independently selected from a halogen C1 to C10 alkyl, C1 to C10 alkyloxy, C1 to C10 alkylthio, optionally substituted phenyl, and C1 to C10 haloalkyl; α is an oxygen atom or a sulfur atom; β is —$(CH_2)_2$—; γ is an oxygen atom or a sulfur atom; b is an integer from 0 to 3, d is an integer from 0 to 4; f, p, and w are each independently an integer from 0 to 5; r is an integer from 0 to 7; and u is an integer from 0 to 4, or $R^9$ is (e) a member of (d) substituted with at least one substituent selected from the group consisting of C1 to C6 alkyl, C1 to C6 alkyloxy, C1 to C6 haloalkyloxy, C1 to C6 haloalkyl, phenyl, and a halogen;
one of $R^7$ and $R^8$ is hydrogen and the other is —$(L^8$—$R^{12}$ wherein $L^3$ is represented by the formula:

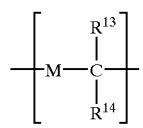

wherein M is —CH—$^2$, —O—, —N($R^{15}$)—, or —S—; $R^{13}$ and $R^{14}$ are each independently a hydrogen atom, C1 to C10 alkyl, aryl, aralkyl, carboxy, or a halogen, and $R^{15}$ is a hydrogen atom or C1 to C6 alkyl; and $R^{12}$ is represented by the formula:

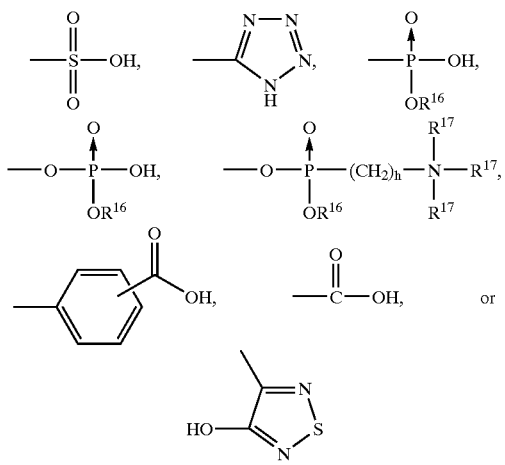

wherein $R^{16}$ is a hydrogen atom, a metal, or C1 to C10 alkyl; $R^{17}$ is independently a hydrogen atom or C1 to C10 alkyl; h is an integer from 1 to 8;

its $C_1$–$C_6$ alkyl, acyloxyalkyl, and alkyloxycarbonyloxyalkyl ester, its pharmaceutically acceptable salt, or hydrate thereof.

3. A compound, its $C_1$–$C_6$ alkyl, acyloxyalkyl, and alkyloxycarbonyloxyalkyl ester, its pharmaceutically acceptable salt, or hydrate thereof as claimed in claim 1, wherein $R^1$ is represented by the formula:

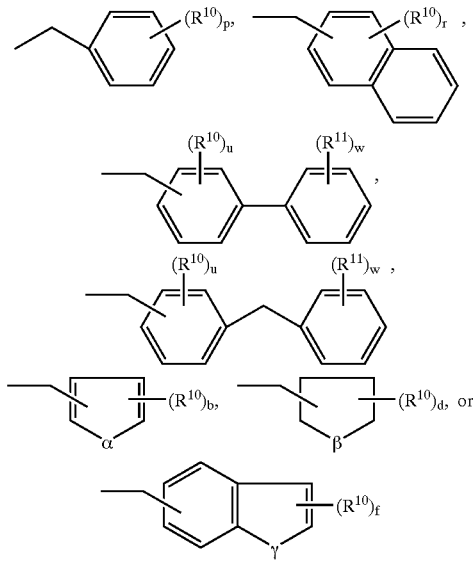

wherein $R^{10}$ and $R^{11}$ are each independently selected from a halogen C1 to C10 alkyl, C1 to C10 alkyloxy, C1 to C10 alkylthio, optionally substituted phenyl, and C1 to C10 haloalkyl; b is an integer from 0 to 3, d is an integer from 0 to 4; f, p, and w are each independently an integer from 0 to 5; r is an integer from 0 to 7; and u is an integer from 0 to 4, or $R^9$ is (e) a member of (d) substituted with at least one substituent selected from the group consisting of C1 to C6 alkyl, C1 to C6 alkyloxy, C1 to C6 haloalkyloxy, C1 to C6 haloalkyl, phenyl, and a halogen; α is an oxygen atom or a sulfur atom; β is —(CH$_2$)$_2$—; and γ is an oxygen atom or a sulfur atom.

4. A compound, its $C_1$–$C_6$ alkyl, acyloxyalkyl, and alkyloxycarbonyloxyalkyl ester, its pharmaceutically acceptable salt or hydrate thereof as claimed in claim 1, wherein $R^1$ is represented by the formula:

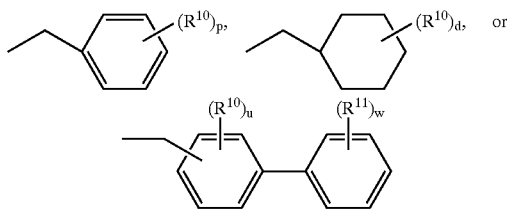

wherein $R^{10}$ and $R^{11}$ are each independently selected from a halogen C1 to C10 alkyl, C1 to C10 alkyloxy, C1 to C10 alkylthio, optionally substituted phenyl, and C1 to C10 haloalkyl; d is an integer from 0 to 4; p and w are each independently an integer from 0 to 5; and u is an integer from 0 to 4, or $R^9$ is (e) a member of (d) substituted with at least one substituent selected from the group consisting of C1 to C6 alkyl, C1 to C6 alkyloxy, C1 to C6 haloalkyloxy, C1 to C6 haloalkyl, phenyl, and a halogen.

5. A compound, its $C_1$–$C_6$ alkyl, acyloxyalkyl, and alkyloxycarbonyloxyalkyl ester, its pharmaceutically acceptable salt, or hydrate thereof as claimed in claim 1, wherein $R^3$ is —O—(CH$_2$)$_m$—COOH (m is as defined above) or —O—CH(—$R^{30}$)—COOH ($R^{30}$ is a hydrogen atom or C1–C3 alkyl).

6. A compound represented by the formula (III):

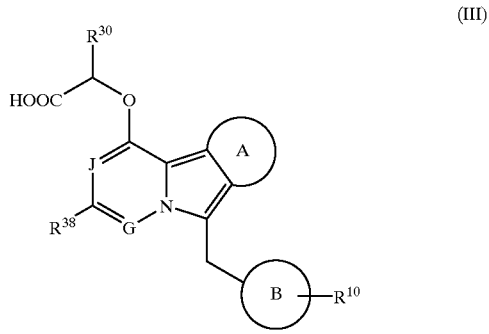

(III)

wherein the A ring G, J, $R^{10}$, and m are as defined in claims 1 and 2; B ring is a benzene ring or a cyclohexane ring; $R^{30}$ and $R^{38}$ are each independently a hydrogen atom or C1–C3 alkyl, its $C_1$–C6 alkyl acyloxyalkyl and alkyloxycarbonyloxyalkyl ester, their pharmaceutically acceptable salt, or hydrate thereof.

7. A compound, its C1–C6 alkyl, acyloxyalkyl, and alkyloxycarbonyloxy ester, its pharmaceutically acceptable salt, or hydrate thereof as claimed in claim 1, wherein said $R^2$ is —COHN$_2$.

8. A compound, its C1–C6 alkyl, acyloxyalkyl, and alkyloxycarbonyloxyalkyl ester, its pharmaceutically acceptable salt, or hydrate thereof as claimed in claim 1, wherein $R^{18}$, $R^{19}$, $R^{20}$, $R^{21}$, $R^{22}$, $R^{23}$, $R^{26}$, and $R^{27}$ are hydrogen atoms.

9. A pharmaceutical composition containing a compound as claimed in claim 1 as an active ingredient.

10. A method of inhibiting the activity of sPLA$_2$, comprising bringing a compound as claimed in claim 1 into contact with sPLA$_2$.

* * * * *